(12) United States Patent
Wong et al.

(10) Patent No.: US 10,765,856 B2
(45) Date of Patent: Sep. 8, 2020

(54) SYSTEMS AND METHODS FOR PERIPHERAL NERVE STIMULATION TO TREAT TREMOR WITH DETACHABLE THERAPY AND MONITORING UNITS

(71) Applicant: Cala Health, Inc., Burlingame, CA (US)

(72) Inventors: Serena HanYing Wong, Palo Alto, CA (US); Kathryn H. Rosenbluth, San Francisco, CA (US); Samuel Richard Hamner, San Francisco, CA (US); Paula Jean Chidester, Menlo Park, CA (US); Scott Lee Delp, Stanford, CA (US); Terence D. Sanger, Los Angeles, CA (US)

(73) Assignee: Cala Health, Inc., Burlingame, CA (US)

( * ) Notice: Subject to any disclaimer, the term of this patent is extended or adjusted under 35 U.S.C. 154(b) by 131 days.

(21) Appl. No.: 15/580,631

(22) PCT Filed: Jun. 10, 2016

(86) PCT No.: PCT/US2016/037080
§ 371 (c)(1),
(2) Date: Dec. 7, 2017

(87) PCT Pub. No.: WO2016/201366
PCT Pub. Date: Dec. 15, 2016

(65) Prior Publication Data
US 2018/0169400 A1    Jun. 21, 2018

Related U.S. Application Data

(60) Provisional application No. 62/173,894, filed on Jun. 10, 2015.

(51) Int. Cl.
*A61N 1/04* (2006.01)
*A61N 1/36* (2006.01)
(Continued)

(52) U.S. Cl.
CPC ......... *A61N 1/0456* (2013.01); *A61N 1/0476* (2013.01); *A61N 1/0484* (2013.01);
(Continued)

(58) Field of Classification Search
CPC .............. A61N 1/0456; A61N 1/36139; A61N 1/36067
(Continued)

(56) References Cited

U.S. PATENT DOCUMENTS 3,204,637 A    9/1965    Frank et al.
3,870,051 A    3/1975    Brindley
(Continued)

FOREIGN PATENT DOCUMENTS

DE    102008042373    4/2010
DE    102009004011    7/2010
(Continued)

OTHER PUBLICATIONS

U.S. Appl. No. 16/071,056, filed Jul. 18, 2018, Wong et al.
(Continued)

*Primary Examiner* — Amanda K Hulbert
*Assistant Examiner* — Philip C Edwards
(74) *Attorney, Agent, or Firm* — Knobbe, Martens, Olson & Bear LLP

(57) ABSTRACT

A system and method for providing therapy to a patient can include a monitoring unit and a therapy unit. The monitoring unit can have a user interface and one or more sensors to measure patient data. The therapy unit can have a stimulator for generating electrical stimulation and a microcontroller
(Continued)

for controlling the generation of the electrical stimulation based on the measured patient data.

16 Claims, 10 Drawing Sheets

(51) Int. Cl.
*A61N 1/32* (2006.01)
*A61N 1/372* (2006.01)

(52) U.S. Cl.
CPC .......... *A61N 1/0496* (2013.01); *A61N 1/321* (2013.01); *A61N 1/36017* (2013.01); *A61N 1/36057* (2013.01); *A61N 1/36067* (2013.01); *A61N 1/36139* (2013.01); *A61N 1/36014* (2013.01); *A61N 1/36125* (2013.01); *A61N 1/37247* (2013.01); *A61N 1/37252* (2013.01)

(58) Field of Classification Search
USPC .......................................................... 607/62
See application file for complete search history.

(56) References Cited

U.S. PATENT DOCUMENTS

| | | |
|---|---|---|
| 4,300,575 A | 11/1981 | Wilson |
| 4,458,696 A | 7/1984 | Larimore |
| 4,461,075 A | 7/1984 | Bailey |
| 4,539,996 A | 9/1985 | Engel |
| 4,569,351 A | 2/1986 | Tang |
| 4,582,049 A | 4/1986 | Ylvisaker |
| 4,729,377 A | 3/1988 | Granek et al. |
| 4,739,764 A | 4/1988 | Lue et al. |
| 4,763,659 A | 8/1988 | Dunseath, Jr. |
| 4,771,779 A | 9/1988 | Tanagho et al. |
| 4,981,146 A | 1/1991 | Bertolucci |
| 4,982,432 A | 1/1991 | Clark et al. |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 6,016,449 A | 1/2000 | Fischell et al. |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,366,813 B1 | 4/2002 | DiLorenzo |
| 6,445,955 B1 | 9/2002 | Michelson et al. |
| 6,449,512 B1 | 9/2002 | Boveja |
| 6,505,074 B2 | 1/2003 | Boveja et al. |
| 6,546,290 B1 | 4/2003 | Shloznikov |
| 6,564,103 B2 | 5/2003 | Fischer et al. |
| 6,579,270 B2 | 6/2003 | Sussman et al. |
| 6,652,449 B1 | 11/2003 | Gross et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,857,771 B2 | 12/2010 | Alwan et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,996,088 B2 | 8/2011 | Marrosu et al. |
| 7,998,092 B2 | 8/2011 | Avni |
| 8,000,796 B2 | 8/2011 | Tass |
| 8,025,632 B2 | 9/2011 | Einarsson |
| 8,046,083 B2 | 10/2011 | Tegenthoff et al. |
| 8,075,499 B2 | 12/2011 | Nathan et al. |
| 8,086,318 B2 | 12/2011 | Strother et al. |
| 8,121,694 B2 | 2/2012 | Molnar et al. |
| 8,145,316 B2 | 3/2012 | Deem et al. |
| 8,165,668 B2 | 4/2012 | Dacey, Jr. et al. |
| 8,175,718 B2 | 5/2012 | Wahlgren et al. |
| 8,187,209 B1 | 5/2012 | Guiffrida et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,301,215 B2 | 10/2012 | Lee |
| 8,306,624 B2 | 11/2012 | Gerber et al. |
| 8,313,443 B2 | 11/2012 | Tom |
| 8,343,026 B2 | 1/2013 | Gardiner et al. |
| 8,364,257 B2 | 1/2013 | Van Den Eerenbeemd et al. |
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,409,116 B2 | 4/2013 | Wang et al. |
| 8,412,338 B2 | 4/2013 | Faltys |
| 8,414,507 B2 | 4/2013 | Asada |
| 8,428,719 B2 | 4/2013 | Napadow |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |

(56) References Cited

U.S. PATENT DOCUMENTS

| | | |
|---|---|---|
| 8,473,064 B2 | 6/2013 | Castel et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | MacHado et al. |
| 9,192,763 B2 | 11/2015 | Gerber et al. |
| 9,220,895 B2 | 12/2015 | Siff et al. |
| 9,227,056 B1 | 1/2016 | Heldman et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,408,683 B2 | 8/2016 | St Anne et al. |
| 9,414,776 B2 | 8/2016 | Sillay et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,597,509 B2 | 3/2017 | Hoffer et al. |
| 9,675,800 B2 | 6/2017 | Li et al. |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B2 | 1/2018 | Giuffrida et al. |
| 9,924,899 B2 | 3/2018 | Pracar et al. |
| 9,974,478 B1 | 5/2018 | Brokaw et al. |
| 9,980,659 B2 | 5/2018 | Sadeghian-Motahar et al. |
| 10,004,900 B2 | 6/2018 | Kent et al. |
| 10,022,545 B1 | 7/2018 | Giuffrida |
| 10,028,695 B2 | 7/2018 | Machado et al. |
| 10,130,809 B2 | 11/2018 | Cartledge et al. |
| 10,173,060 B2 | 1/2019 | Wong et al. |
| 10,179,238 B2 | 1/2019 | Wong et al. |
| 10,213,602 B2 | 2/2019 | Ironi et al. |
| 10,549,093 B2 | 2/2020 | Wong et al. |
| 10,561,839 B2 | 2/2020 | Wong et al. |
| 10,603,482 B2 | 3/2020 | Hamner et al. |
| 10,625,074 B2 | 4/2020 | Rosenbluth et al. |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0127939 A1 | 7/2004 | Grey et al. |
| 2004/0133249 A1* | 7/2004 | Gesotti ............. A61N 1/36003 607/48 |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0234309 A1 | 10/2005 | Klapper |
| 2006/0047326 A1 | 3/2006 | Wheeler |
| 2006/0052726 A1 | 3/2006 | Weisz et al. |
| 2006/0095088 A1 | 5/2006 | De Ridder |
| 2006/0161218 A1 | 7/2006 | Danilov |
| 2006/0173509 A1 | 8/2006 | Lee et al. |

(56) References Cited

U.S. PATENT DOCUMENTS

| | | |
|---|---|---|
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0207193 A1 | 9/2007 | Zasler et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0058773 A1 | 3/2008 | John |
| 2008/0058893 A1 | 3/2008 | Noujokat |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208288 A1 | 8/2008 | Podrazhansky et al. |
| 2008/0216593 A1 | 9/2008 | Jacobsen et al. |
| 2008/0288016 A1 | 11/2008 | Amurthur et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0247910 A1 | 10/2009 | Klapper |
| 2009/0299435 A1 | 12/2009 | Gliner et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0010381 A1 | 1/2010 | Skelton et al. |
| 2010/0010572 A1 | 1/2010 | Skelton et al. |
| 2010/0057154 A1 | 3/2010 | Dietrich et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0202107 A1 | 8/2011 | Sunagawa et al. |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0301663 A1 | 12/2011 | Wang et al. |
| 2012/0010492 A1 | 1/2012 | Thramann et al. |
| 2012/0053491 A1 | 3/2012 | Nathan et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0220812 A1 | 8/2012 | Mishelevich |
| 2012/0239112 A1 | 9/2012 | Muraoka |
| 2012/0259255 A1 | 10/2012 | Tomlinson et al. |
| 2012/0277621 A1 | 11/2012 | Gerber et al. |
| 2012/0302821 A1 | 11/2012 | Burnett |
| 2012/0310298 A1 | 12/2012 | Besio et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0158624 A1 | 6/2013 | Bain et al. |
| 2013/0158627 A1 | 6/2013 | Gozani et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0214119 A1 | 7/2014 | Greiner et al. |
| 2014/0228927 A1 | 8/2014 | Ahmad et al. |
| 2014/0236258 A1* | 8/2014 | Carroll .............. A61N 1/36021 607/46 |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |

(56) References Cited

U.S. PATENT DOCUMENTS

| | | |
|---|---|---|
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0321000 A1 | 11/2015 | Rosenbluth et al. |
| 2015/0335882 A1 | 11/2015 | Gross et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0220836 A1 | 8/2016 | Parks |
| 2016/0262685 A1 | 9/2016 | Wagner et al. |
| 2016/0287879 A1 | 10/2016 | Denison et al. |
| 2016/0039239 A1 | 11/2016 | Yoo et al. |
| 2016/0339239 A1 | 11/2016 | Yoo et al. |
| 2017/0014625 A1 | 1/2017 | Rosenbluth et al. |
| 2017/0027812 A1 | 2/2017 | Hyde et al. |
| 2017/0056238 A1 | 3/2017 | Yi et al. |
| 2017/0079597 A1 | 3/2017 | Horne |
| 2017/0080207 A1 | 3/2017 | Perez et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2018/0049676 A1 | 2/2018 | Griffiths et al. |
| 2018/0064344 A1 | 3/2018 | Nguyen |
| 2018/0064944 A1 | 3/2018 | Grill et al. |
| 2018/0168905 A1 | 6/2018 | Goodall et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0264263 A1 | 9/2018 | Rosenbluth et al. |
| 2019/0001117 A1 | 1/2019 | Ben-David et al. |
| 2019/0001129 A1 | 1/2019 | Rosenbluth et al. |
| 2019/0134393 A1 | 5/2019 | Wong et al. |
| 2020/0093400 A1 | 3/2020 | Hamner et al. |

FOREIGN PATENT DOCUMENTS

| | | |
|---|---|---|
| EP | 0000759 | 2/1979 |
| EP | 0725665 | 1/1998 |
| EP | 1062988 | 12/2000 |
| EP | 1558333 | 5/2007 |
| EP | 2383014 | 11/2011 |
| EP | 2801389 | 11/2014 |
| EP | 3020448 | 5/2016 |
| ES | 2222819 | 3/2006 |
| ES | 2272137 | 6/2008 |
| GB | 2496449 | 5/2013 |
| JP | 2002/200178 | 7/2002 |
| JP | 2003-501207 | 1/2003 |
| JP | 2006-503658 | 2/2006 |
| JP | 2008/018235 | 1/2008 |
| JP | 2009/34328 | 2/2009 |
| JP | 2009/529352 | 8/2009 |
| JP | 2010/506618 | 3/2010 |
| JP | 2010/512926 | 4/2010 |
| JP | 2012/005596 | 1/2012 |
| JP | 2012/055650 | 3/2012 |
| JP | 2013/017609 | 1/2013 |
| JP | 2013/094305 | 5/2013 |
| JP | 54-39921 | 3/2014 |
| WO | WO1994/000187 | 1/1994 |
| WO | WO1994/017855 | 8/1994 |
| WO | WO1996/032909 | 10/1996 |
| WO | WO1998/043700 | 10/1998 |
| WO | WO1999/019019 | 4/1999 |
| WO | WO2000/015293 | 3/2000 |
| WO | WO2002/017987 | 3/2002 |
| WO | WO2005/122894 | 12/2005 |
| WO | WO2007/112092 | 10/2007 |
| WO | WO2009/153730 | 12/2009 |
| WO | WO2010/111321 | 9/2010 |
| WO | WO2010/141155 | 12/2010 |
| WO | WO2011/119224 | 9/2011 |
| WO | WO2011/144883 | 11/2011 |
| WO | WO2012/040243 | 3/2012 |
| WO | WO2013/071307 | 5/2013 |
| WO | WO2013/074809 | 5/2013 |
| WO | WO2014/043757 | 3/2014 |
| WO | WO2014/053041 | 4/2014 |
| WO | WO2014/113813 | 7/2014 |
| WO | WO2014/146082 | 9/2014 |
| WO | WO2014/151431 | 9/2014 |
| WO | WO2014/153201 | 9/2014 |
| WO | WO2014/207512 | 12/2014 |
| WO | WO2015/033152 | 3/2015 |
| WO | WO2015/039206 | 3/2015 |
| WO | WO2015/039244 | 3/2015 |
| WO | WO2015/042365 | 3/2015 |
| WO | WO2015/079319 | 6/2015 |
| WO | WO2015/095880 | 6/2015 |
| WO | WO2015/128090 | 9/2015 |
| WO | WO2015/164706 | 10/2015 |
| WO | WO2015/187712 | 12/2015 |
| WO | WO2016/007093 | 1/2016 |
| WO | WO2016/019250 | 2/2016 |
| WO | WO2016/094728 | 6/2016 |
| WO | WO2016/102958 | 6/2016 |
| WO | WO2016/110804 | 7/2016 |
| WO | WO2016/128985 | 8/2016 |
| WO | WO2016/149751 | 9/2016 |
| WO | WO2016/166281 | 10/2016 |
| WO | WO2016/179407 | 11/2016 |
| WO | WO2016/189422 | 12/2016 |
| WO | WO2016/195587 | 12/2016 |
| WO | WO2016/201366 | 12/2016 |
| WO | WO2017/004021 | 1/2017 |
| WO | WO2017/010930 | 1/2017 |
| WO | WO2017/023864 | 2/2017 |
| WO | WO2017/053847 | 3/2017 |

(56) References Cited

FOREIGN PATENT DOCUMENTS

| | | |
|---|---|---|
| WO | WO2017/062994 | 4/2017 |
| WO | WO2017/086798 | 5/2017 |
| WO | WO2017/088573 | 6/2017 |
| WO | WO2017/132067 | 8/2017 |
| WO | WO2017/199026 | 11/2017 |
| WO | WO2017/208167 | 12/2017 |
| WO | WO2017/209673 | 12/2017 |
| WO | WO2017/210729 | 12/2017 |
| WO | WO2017/221037 | 12/2017 |
| WO | WO2018/009680 | 1/2018 |
| WO | WO2018/028170 | 2/2018 |
| WO | WO2018/028220 | 2/2018 |
| WO | WO2018/028221 | 2/2018 |
| WO | WO2018/039458 | 3/2018 |
| WO | WO2018/093765 | 5/2018 |
| WO | WO2018/112164 | 6/2018 |
| WO | WO2018/187241 | 10/2018 |
| WO | WO2019/005774 | 1/2019 |
| WO | WO2019/014250 | 1/2019 |
| WO | WO 2019/143790 | 7/2019 |
| WO | WO 2019/213433 | 11/2019 |
| WO | WO 2020/006048 | 1/2020 |
| WO | WO 2020/069219 | 4/2020 |
| WO | WO 2020/086726 | 4/2020 |

OTHER PUBLICATIONS

U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
Apartis; Clinical neurophysiology in movement disorders. Handb Clin Neurol; 111; Pediatric Neurology Pt. 1; pp. 87-92;Apr. 2013.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.

Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006—Part 1.
Buschbacher et al.; Manual of nerve conduction series; 2nd edition; Demos Medical Publishing, LLC; 2006—Part 2.
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et al; Consensus statement of the Movement Disorder Society on Tremor. Ad Hoc Scientific Committee., Movement Disorders, vol. 13 Suppl 3, pp, 2-23; (year of pub. sufficiently earlier than effective US filed and any foreign priority date)1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Extended European Search Report dated Oct. 12, 2018 in European Application No. 16808473.9 in 6 pages.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.

(56) References Cited

OTHER PUBLICATIONS

Gallego et al; A soft wearable robot for tremor assessment and suppression; 2011 IEEE International Conference on Robotics and Automation; Shanghai International Conference Center; pp. 2249-2254; May 9-13, 2011.

Gallego et al.; Real-time estimation of pathological tremor parameters from gyroscope data.; Sensors; 10(3); pp. 2129-2149; Mar. 2010.

Gao; Analysis of amplitude and frequency variations of essential and Parkinsonian tremors; Medical & Biological Engineering & Computing; 42(3); pp. 345-349; May 2004.

Garcia et al.; Modulation of brainstem activity and connectivity by respiratory-gated auricular vagal afferent nerve stimulation in migraine patients; Pain; International Association for the Study of Pain; 2017.

Garcia-Rill, E., et al. "Arousal, motor control, and Parkinson's disease." Translational neuroscience 6.1 pp. 198-207 (2015).

Giuffridda et al.; Clinically deployable Kinesia technology for automated tremor assessment.; Movement Disorders; 24(5); pp. 723-730; Apr. 2009.

Gracanin et al.; Optimal stimulus parameters for minimum pain in the chronic stimulatin of innervated muscle; Archives of Physical Medicine and Rehabilitation; 56(6); pp. 243-249; Jun. 1975.

Haeri et al.; Modeling the Parkinson's tremor and its treatments; Journal of Theoretical Biology; 236(3); pp. 311-322; Oct. 2005.

Halon EN et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.

Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.

Hauptmann et al.; External trial deep brain stimulation device for the application of desynchronizing stimulation techniques; Journal of Neural Engineering; 6; 12 pgs.; Oct. 2009.

Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.

Henry Dreyfuss Associates; The Measure of Man and Woman: Human Factors in Design (Revised Edition); John Wiley & Sons, New York; pp. 10-11 and 22-25; Dec. 2001.

Hernan, Miguel, et al. "Alcohol Consumption and the Incidence of Parkinson's Disease." May 15, 2003. Annals of Neurology. Vol. 54. pp. 170-175.

Hua et al.; Posture-related oscillations in human cerebellar thalamus in essential tremor are enabled by voluntary motor circuits; J Neurophysiol; 93(1); pp. 117-127; Jan. 2005.

Huang, et al.; Theta burst stimulation report of the human motor cortex; Neuron, vol. 45, 201-206, Jan. 20, 2005.

Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.

Hubeaux, Katelyne, et al. "Evidence for autonomic nervous system dysfunction in females with idiopathic overactive bladder syndrome." Neurourology and urodynamics 30.8 (2011): 1467-1472.

Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.

Jacks et al.; Instability in human forearm movements studied with feed-back-controlled electrical stimulation of muscles; Journal of Physiology; 402; pp. 443-461; Aug. 1988.

Jobges et al.; Vibratory proprioceptive stimulation affects Parkinsonian tremor; Parkinsonism & Related Disorders; 8(3); pp. 171-176; Jan. 2002.

Joundi et al.; Rapid tremor frequency assessment with the iPhone accelerometer.; Parkinsonism & Related Disorders; 17(4); pp. 288-290; May 2011.

Kim et al.: Adaptive control of movement for neuromuscular stimulation-assisted therapy in a rodent model; IEEE Trans on Biomedical Engineering,; 56(2); pp. 452-461; Feb. 2009.

Krauss et al.; Chronic spinal cord stimulation in medically intractable orthostatic tremor; J Neurol Neurosurg Psychiatry; 77(9); pp. 1013-1016; Sep. 2006.

Kuhn et al.; Array electrode design for transcutaneous electrical stimulation a simulation study; Medical Engineering & Physics; 31 (8); pp. 945-951; Oct. 2009.

Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.

Kunz, Patrik, et al. "5 kHz transcranial alternating current stimulation: lack of cortical excitability changes when grouped in a theta burst pattern." Frontiers in Human Neuroscience 10 (2016): 683.

Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.

Laroy et al.; The sensory innervation pattern of the fingers; J. Neurol.; 245 (5); pp. 294-298; May 1998.

Lee et al.; Resetting of tremor by mechanical perturbations: A comparison of essential tremor and parkinsonian tremor; Annals of Nuerology; 10(6); pp. 523-531; Dec. 1981.

Legon et al.; Pulsed ultrasound differentially stimulates somatosensory circuits in humans as indicated by EEG and fMRI; PLoS One; 7(12); e51177; 14 pgs.; Dec. 2012.

Liao, Wen☐Chien, et al. "A noninvasive evaluation of autonomic nervous system dysfunction in women with an overactive bladder." International Journal of Gynecology & Obstetrics 110.1 (2010): 12-17.

Lourenco et al.; Effects produced in human arm and forearm motoneurones after electrical stimulation of ulnar and median nerves at wrist level; Experimental Brain Research; 178(2); pp. 267-284; Apr. 2007.

Malek et al.; The utility of electromyography and mechanomyography for assessing neuromuscular function: a noninvasive approach; Phys Med Rehabil in N Am; 23(1); pp. 23-32; Feb. 2012.

Mamorita et al.; Development of a system for measurement and analysis of tremor using a three-axis accelerometer; Methods Inf Med; 48(6); pp. 589-594; epub Nov. 2009.

Maneski et al.; Electrical Stimulation for suppression of pathological tremor; Med Biol Eng Comput; 49(10); pp. 1187-1193; Oct. 2011.

Marsden et al.; Coherence between cerebellar thalamus, cortex and muscle in man; Brain; 123; pp. 1459-1470; Jul. 2000.

Marshall, Ryan, et al. "Bioelectrical stimulation for the reduction of inflammation in inflammatory bowel disease." Clinical Medicine Insights: Gastroenterology 8 (2015): CGast-S31779.

McAuley et al.; Physiological and pathological tremors and rhythmic central motor control; Brain; 123(Pt 8); pp. 1545-1567; Aug. 2000.

McIntyre et al.; Finite element analysis of current-density and electric field generated by metal microelectrodes; Annals of Biomedical Engineering; 29(3); pp. 227-235; Mar. 2001.

Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.

Mehnert, Ulrich, et al. "Heart rate variability: an objective measure of autonomic activity and bladder sensations during urodynamics." Neurourology and urodynamics 28.4 (2009): 313-319.

Miguel et al.; Alcohol consumption and the incidence of Parkinson's disease; Ann. Neurol.; 54(2); pp. 170-175; May 15, 2003.

Miller et al.; Multiplexed microneedle-based biosensor array for characterization of metabolic acidosis; Talanta; 88; pp. 739-742; Jan. 2012 (author manuscript; 13 pgs.).

Miller et al.; Neurostimulation in the treatment of primary headaches; Pract Neurol; Apr. 11, 2016;16:pp. 362-375.

(56) References Cited

OTHER PUBLICATIONS

Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp, 528-531; Dec. 2007.
Munhoz et al; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
PCT Search Report and Written Opinion in PCT Application No. PCT/US2016/037080 dated Sep. 13, 2016 in 11 pages.
Perez et al.; Patterned Sensory Stimulation Induces Plasticity in Reciprocal la Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popović☐Bijelić, Ana, et al. "Multi☐field surface electrode for selective electrical stimulation." Artificial organs 29.6 (2005): 448-452.
Popovi Maneski et al.; Electrical stimulation for the suppression of pathological tremor; Medical & Biological Engineering & Computing; 49(10); pp. 1187-1193; Oct. 2011.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-S8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Silverstone et al.; Non-Invasive Neurostimulation in the Control of Familial Essential Tremor Using the Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Toloso et al.; Essential tremor: treatment with propranolol; Neurology; 25(11); pp. 1041; Nov. 1975.
Tracey; The inflammatory reflex; Nature; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecallncontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
PCT/US2014/012388 (published as WO 2014/113813), Jan. 21, 2014.
U.S. Appl. No. 14/805,385 (now U.S. Pat. No. 9,452,287), filed Jul. 21, 2015.
U.S. Appl. No. 15/277,946 (published as U.S. Pub. No. 2017/0014625), filed Sep. 27, 2016.
U.S. Appl. No. 15/983,024 (now U.S. Pat. No. 10,625,074), filed May 17, 2018.
U.S. Appl. No. 16/020,876 (published as 2019/0001129), filed Jun. 27, 2018.
PCT/US2019/039193 (published as PCT Pub. No. WO 2020/006048), Jun. 26, 2019.
U.S. Appl. No. 14/271,669 (published as U.S. Pub. No. 2014/0336722), filed Nov. 13, 2014.
PCT/US2015/033809 (published as WO 2015/187712), Jun. 2, 2015.
U.S. Appl. No. 15/354,943 (now U.S. Pat. No. 9,802,041), filed Nov. 17, 2016.
U.S. Appl. No. 15/721,475 (now U.S. Pat. No. 10,179,238), filed Sep. 29, 2017.
U.S. Appl. No. 15/721,480 (now U.S. Pat. No. 10,173,060), filed Sep. 29, 2017.

(56) References Cited

OTHER PUBLICATIONS

U.S. Appl. No. 16/242,983 (now U.S. Pat. No. 10,549,093), filed Jan. 8, 2019.
U.S. Appl. No. 16/247,310 (now U.S. Pat. No. 10,561,839), filed Jan. 14, 2019.
U.S. Appl. No. 16/780,758, filed Feb. 3, 2020.
U.S. Appl. No. 16/792,100, filed Feb. 14, 2020.
PCT/US2016/037080 (published as WO 2016/201366), Jun. 10, 2016.
PCT/US2017/014431 (published as WO 2017/132067), Jan. 20, 2017.
PCT/US2018/025752 (published as WO 2018/187241), Apr. 2, 2018.
U.S. Appl. No. 16/071,056, filed Jul. 18, 2018.
PCT/US2016/045038 (published as WO 2017/023864), Aug. 1, 2016.
U.S. Appl. No. 15/748,616, filed Jan. 29, 2018.
PCT/US2016/053513 (published as WO 2017/053847), Sep. 23, 2016.
U.S. Appl. No. 15/762,043 (now U.S. Pat. No. 10,603,482), filed Mar. 21, 2018.
U.S. Appl. No. 16/833,388, filed Mar. 27, 2020.
PCT/US2017/040920 (published as WO 2018/009680), Jul. 6, 2017.
U.S. Appl. No. 16/241,846 (published as U.S. Pub. No. 2019/0134393), filed Jan. 7, 2019.
PCT/US2017/048424 (published as WO 2018/039458), Aug. 24, 2017.
U.S. Appl. No. 16/327,780, filed Feb. 22, 2019.
PCT/US2019/013966 (published as WO 2019/143790), Jan. 17, 2019.
PCT/US2019/030458 (published as WO 2019/213433), May 2, 2019.
PCT/US2019/053297 (published as WO 2020/069219), Sep. 26, 2019.
PCT/US2019/057674 (published as WO 2020/086726), Oct. 23, 2019.

* cited by examiner

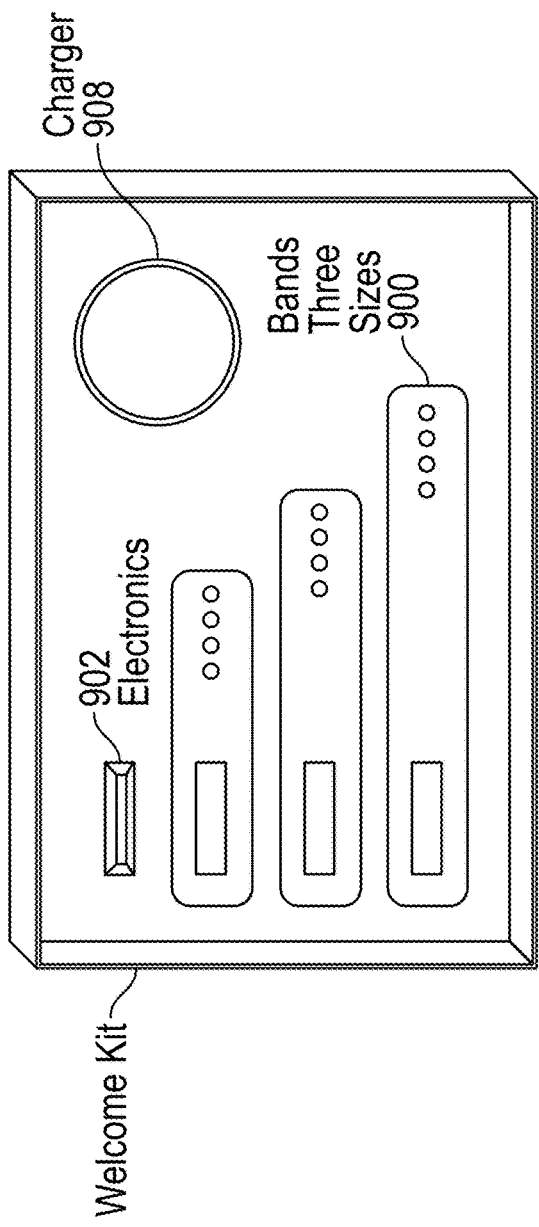
FIG. 9B
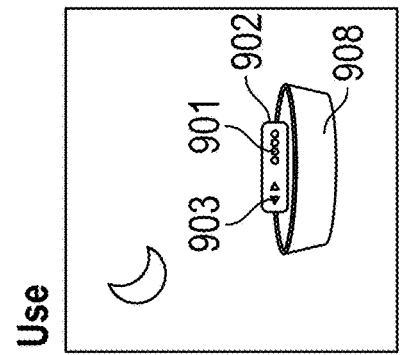
Daily Use
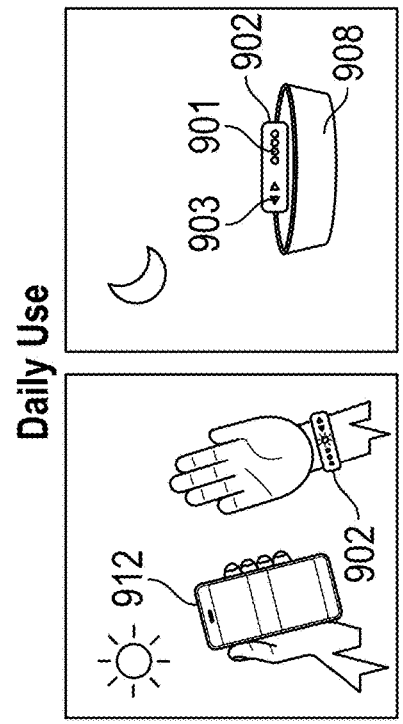
FIG. 9D
FIG. 9E
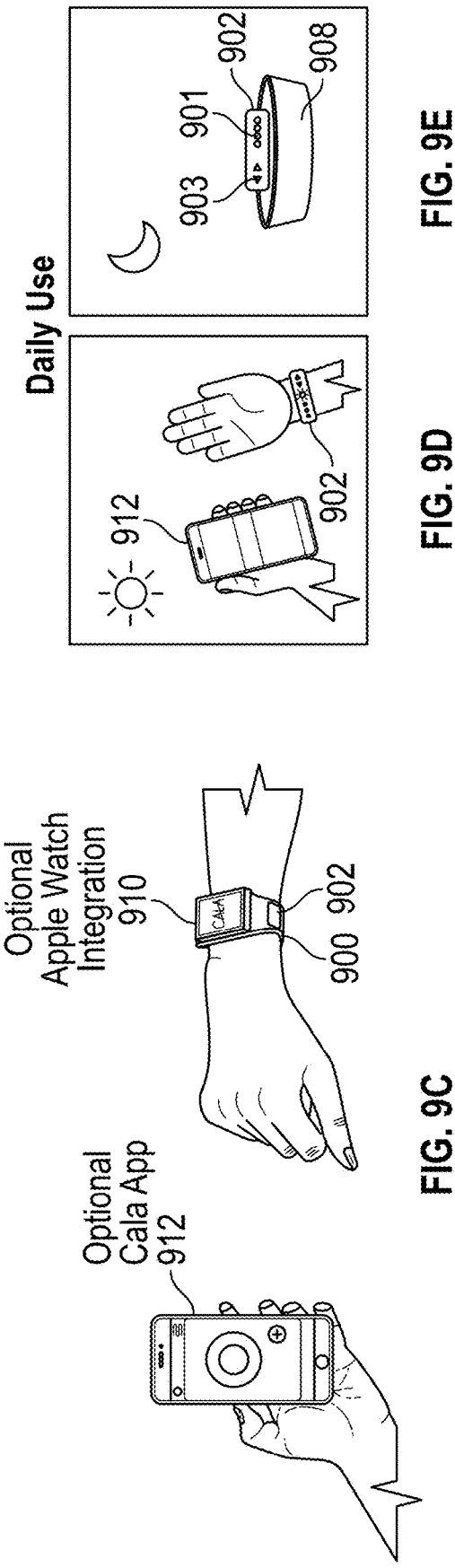
FIG. 9C

SYSTEMS AND METHODS FOR PERIPHERAL NERVE STIMULATION TO TREAT TREMOR WITH DETACHABLE THERAPY AND MONITORING UNITS

CROSS REFERENCE TO RELATED APPLICATIONS

This application is the U.S. National Stage under 35 U.S.C. § 371 of PCT Applications. No. PCT/US2016/037080 filed on Jun. 10, 2016, which in turn claims priority to U.S. Provisional Application No. 62/173,894, filed Jun. 10, 2015, each of the foregoing of which are herein incorporated by reference in their entireties.

INCORPORATION BY REFERENCE

U.S. Patent Publication No. 2015/0321000, filed Jul. 21, 2015, and International Publication No. WO2015/187712, filed Jun. 2, 2015, and herein incorporated by reference in their entireties for all purposes.

All publications and patent applications mentioned in this specification are herein incorporated by reference to the same extent as if each individual publication or patent application was specifically and individually indicated to be incorporated by reference.

FIELD

Embodiments of the invention relate generally to systems and methods for treating a disease or disorder, and more specifically to systems and method for treating a disease or disorder, such as tremor, using a monitoring unit and a therapy unit.

BACKGROUND

Essential tremor (ET) is the most common movement disorder, affecting an estimated 10 million patients in the U.S., with growing numbers due to the aging population. The prevalence increases with age, increasing from 6.3% of the population over 65, to above 20% over 95. ET is characterized by oscillatory movement, for example between 4-12 Hz, affecting distal limbs, especially the hands. Unlike Parkinson's tremor, which exists at rest, essential tremor is postural and kinetic, meaning tremor is induced by holding a limb against gravity or during movement respectively.

Disability with ET is common, and varies from embarrassment to the inability to live independently as key tasks such as writing and self-feeding are not possible due to the uncontrolled movement. Despite the high disability and prevalence of ET, there are insufficient treatment options to address tremor. Drugs used to treat tremor (e.g., Propranolol and Primidone) have been found to be ineffective in 40% of patients and only reduces tremor by 50%. These drugs also have side effects that can be severe. The alternative treatment is surgical implantation of a deep brain stimulator, which can be effective in reducing tremor amplitude by 90%, but is a highly invasive surgical procedure that carries significant risks and cannot be tolerated by many ET patients. There is thus a great need for alternative treatments for ET patients.

Tremor is also a significant problem for patients with orthostatic tremor, multiple sclerosis and Parkinson's disease. The underlying etiology of tremor in these conditions differs from ET, however treatment options for these conditions are also limited and alternative treatment is warranted.

A number of conditions, such as tremors, can be treated through some form of transcutaneous peripheral nerve stimulation. People have a wide variation in wrist diameters, nerve locations, nerve depolarization characteristics, and skin conduction that leads to challenges in designing a device to comfortably, safely and reliably stimulate the peripheral nerves across a broad population of potential users. For instance, in a wrist-worn device targeting the median, ulnar, and radial nerves at the wrist, the amount of power needed for a given stimulation session can vary widely based on skin impedance and usage scenarios.

SUMMARY OF THE DISCLOSURE

The present invention relates generally to systems and methods for treating a disease or disorder, and more specifically to systems and method for treating a disease or disorder, such as tremor, using a monitoring unit and a therapy unit.

The devices and methods of this disclosure each have several innovative aspects, no single one of which is solely responsible for the desirable attributes disclosed herein. The present application discloses devices and methods for reducing tremor in a subject. In some embodiments, a device is provided. The device can include a housing and one or more affectors, power sources, or controls. In some embodiments, the device further includes one or more sensors. Further aspects and embodiments of the present invention are set forth herein.

These and other aspects and embodiments of the invention are described in greater detail below, with reference to the drawing figures.

In some embodiments, a system for treating tremor of a patient is provided. The system can include a band and a detachable therapy unit. The band can have at least two electrodes, a receptacle, and a first electrical circuit in electrical communication with both the at least two electrodes and the receptacle. The detachable therapy unit can include a second electrical circuit; one or more sensors in electrical communication with the second electrical circuit, the one or more sensors configured to measure data from the patient; a stimulator configured to generate an electrical stimulation, the stimulator in electrical communication with the second electrical circuit; at least two electrodes that are configured to receive the electrical stimulation from the stimulator; a controller configured to control the generation of the electrical stimulation by the stimulator; and a power source in electrical communication with the second electrical circuit; wherein the detachable therapy unit is configured to be reversibly attached to the receptacle of the band such that the at least two electrodes are in electrical communication with the stimulator.

In some embodiments, the band further includes one or more identifiers.

In some embodiments, the one or more identifiers are associated with stimulation parameters and/or usage life information.

In some embodiments, the system further includes a base station configured to charge the power source. In some embodiments, the base station is further configured to receive and transmit data to and from the detachable therapy unit and to and from a cloud computing network.

In some embodiments, the system further includes an online portal, such as a physician web portal, configured to access the data stored on the cloud computing network.

In some embodiments, the system further includes an online portal, such as a physician web portal, configured to provide information and parameter changes back to the detachable therapy unit.

In some embodiments, the system further includes a portable computing device with a second user interface and a display, wherein the portable computing device is configured to wirelessly communicate with the detachable therapy unit and to receive data from the cloud computing network.

In some embodiments, the receptacle comprises a securement feature for reversibly attaching the detachable therapy unit to the receptacle.

In some embodiments, the securement feature is selected from the group consisting of a clip, a magnet, a snap fit mechanism, a twist fit mechanism, a screw mechanism, a latching mechanism, a sliding mechanism, a flexible lip, and a hook.

In some embodiments, the detachable therapy unit further comprises a user interface.

In some embodiments, the controller is configured to control the generation of the electrical stimulation by the stimulator based on data measured by the one or more sensors.

In some embodiments, a system for treating tremor of a patient is provided. The system can include a wearable monitoring unit and a first therapy unit. The wearable monitoring unit can include an electrical circuit; one or more sensors in electrical communication with the electrical circuit, the one or more sensors configured to measure data from the patient; at least two electrodes. The first therapy unit can include a power source; a stimulator powered by the power source, the stimulator configured to generate an electrical stimulation that is delivered through the at least two electrodes of the wearable monitoring unit; and a controller configured to control the generation of the electrical stimulation by the stimulator based on data measured by the one or more sensors; wherein the first therapy unit is reversibly attachable to the wearable monitoring unit.

In some embodiments, the system further includes a second therapy unit. The second therapy unit can include a second power source, wherein the second power source of the second therapy unit has more electrical capacity than the power source of the first therapy unit; a second stimulator powered by the second power source, the second stimulator configured to generate an electrical stimulation that is delivered through the at least two electrodes of the wearable monitoring unit; and a second controller configured to control the generation of the electrical stimulation by the stimulator based on data measured by the one or more sensors; wherein the second therapy unit is reversibly attachable to the wearable monitoring unit.

In some embodiments, the one or more sensors are configured to measure motion data. In some embodiments, the controller is configured to determine the tremor frequency, amplitude, and/or phase from the motion data; and control the generation of the electrical stimulation by the stimulator based on the determined tremor frequency, amplitude, and/or phase.

In some embodiments, the at least two electrodes are disposed on a band. In some embodiments, at least one of the at least two electrodes is disposed on a band that is attached to a housing of the wearable monitoring unit and at least one of the at least two electrodes is disposed on a skin facing side of the housing of the wearable monitoring unit.

In some embodiments, a system for treating tremor of a patient is provided. The system can include a wearable monitoring unit and a therapy unit. The wearable monitoring unit can include a user interface; an electrical circuit in electrical communication with the user interface; and one or more sensors in electrical communication with the electrical circuit, the one or more sensors configured to measure data from the patient. The therapy unit can include a stimulator configured to generate an electrical stimulation; at least two electrodes that are configured to receive the electrical stimulation from the stimulator; a controller configured to control the generation of the electrical stimulation by the stimulator based on data measured by the one or more sensors; and a power source disposed within the wearable monitoring unit or the therapy unit; wherein the therapy unit is reversibly attachable to the wearable monitoring unit.

In some embodiments, the wearable monitoring unit is a smart watch.

In some embodiments, the one or more sensors are configured to measure motion data. In some embodiments, the controller is configured to determine the tremor frequency, amplitude, and/or phase from the motion data; and control the generation of the electrical stimulation based on the determined tremor frequency, amplitude, and/or phase.

In some embodiments, the controller is configured to provide automatic and/or manual control of the electrical stimulation.

In some embodiments, the wearable monitoring unit further includes a controller configured to determine the tremor frequency, amplitude, and/or phase from the motion data, and the controller of the therapy unit is configured to control the generation of the electrical stimulation by the stimulator based on the determined tremor frequency, amplitude, and/or phase.

In some embodiments, the at least two electrodes are disposed on a band. In some embodiments, at least one of the at least two electrodes is disposed on a band that is attached to a housing of the therapy unit and at least one of the at least two electrodes is disposed on a skin facing side of the housing of the therapy unit.

In some embodiments, the therapy unit communicates wirelessly with the wearable monitoring unit.

In some embodiments, both the therapy unit and the wearable monitoring unit each have a power source.

In some embodiments, the at least two electrodes are covered with a porous, compressible material that is impregnated with a conductive gel, wherein the porous, compressible material is configured to release the conductive gel when pressure is applied to the porous, compressible material.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 9A-9I illustrate another embodiment of a wearable therapy system.

DETAILED DESCRIPTION

Embodiments of the invention include a device and system and method to measure and collect motion and biological data (e.g., heart rate, galvanic skin response, temperature, and characteristics of the motion disorder, such as tremor frequency, amplitude, and phase), analyze the data as to interpret how these measures may influence motion disorders such as tremor or freezing of gait, and provide peripheral nerve stimulation that targets one or more individual nerves to reduce tremor or initiate gait, where the stimulation applied may or may not be modified based on the measured data.

Embodiments of the therapy system can include three components: (1) a monitoring unit having sensors, circuitry, and optionally may have a power source and/or a microcontroller, (2) a therapy unit having a stimulator (e.g., a pulse generator), circuitry, a power source and a microcontroller, and (3) a skin interface having electrodes and electrical connections for electrically connecting the electrodes to the therapy unit. In some embodiments, all three components are separate components that can be reversibly attached to each other to form a wearable therapy system. In some embodiments, any two of the components can be combined or integrated together to form a wearable two part system that can be reversibly attached to each other. It should be noted that some functions can crossover, such as the electrodes of the skin interface being used as sensors to measure electrical activity (e.g. EMG and ECG) and impedance, for example. In some embodiments, any one of the detachable components can be disposable and/or can be sent back to the manufacturer for recycling.

Figure 1A:
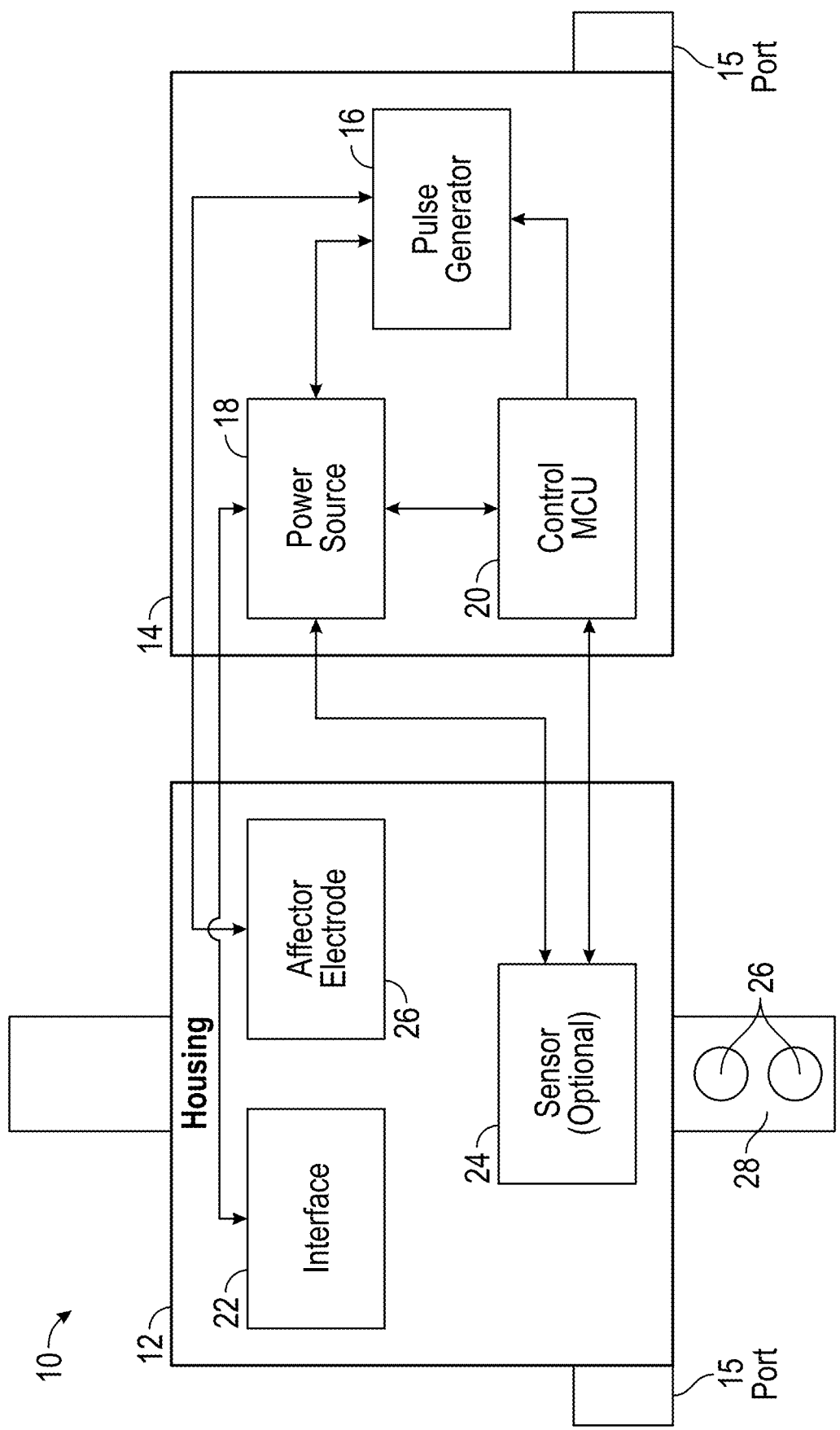
FIGS. 1A and 1B illustrate various embodiments of a monitoring unit and a therapy unit that form a two part treatment system.

One embodiment, as shown in FIG. 1A, is a two-part system 10 including a 1) a monitor unit 12 that can be wearable in some embodiments and 2) a therapy unit 14. In some embodiments, the therapy unit 14 can be can be detachable and can be reversibly attached to the wearable monitor unit 12. The therapy unit 14 may contain an electrical stimulation signal generator 16, power source 18, and a microprocessor and/or microcontroller 20 to control the stimulation. The therapy unit 14 can reversibly connect and communicate directly and/or wirelessly to the wearable monitor 12. In some embodiments, the therapy unit 14 may remain separate from the wearable monitor unit 12 and can communicate wirelessly with the wearable monitor unit 12. In some embodiments, the therapy unit 14 can have a data/power port 15, such as a USB port that allows a user to charge the power source 18, update the software and/or parameters on the microcontroller 20, and/or retrieve data from memory on the wearable monitor unit 12 and/or therapy unit 14. In some embodiments, the data/power port can be located on the wearable monitor unit 12 or both the wearable monitor unit 12 and therapy unit 14. In some embodiments, the wearable monitor unit 12 and/or therapy unit 14 can communicate wirelessly with an external computing device to update the software and/or parameters and/or retrieve data.

In some embodiments, the wearable monitor unit 12 can have a housing with a user interface 22 that encloses one or more sensors 24. In some embodiments, the wearable monitor 12 can be used to detect and/or measure tremor. In some embodiments, the wearable monitor 12 can have one or more electrodes 26 located on the base of the housing that makes contact with the patient's skin. In addition or alternatively, the wearable monitor 12 can have a band 28 or other securement feature with one or more electrodes on the skin facing side of the band 28. In some embodiments, the wearable monitor unit 12 has 2 or 3 electrodes, or at least 2 or 3 electrodes. In some embodiments, the wearable monitor unit 12 lacks a power source and relies on the power source 18 in the therapy unit 14 for power. In other embodiments, both the wearable monitor unit 12 and the therapy unit 14 have power sources. In some embodiments, only the wearable monitor unit 12 has a power source and the therapy unit relies on power from the monitoring unit.

Figure 1B:
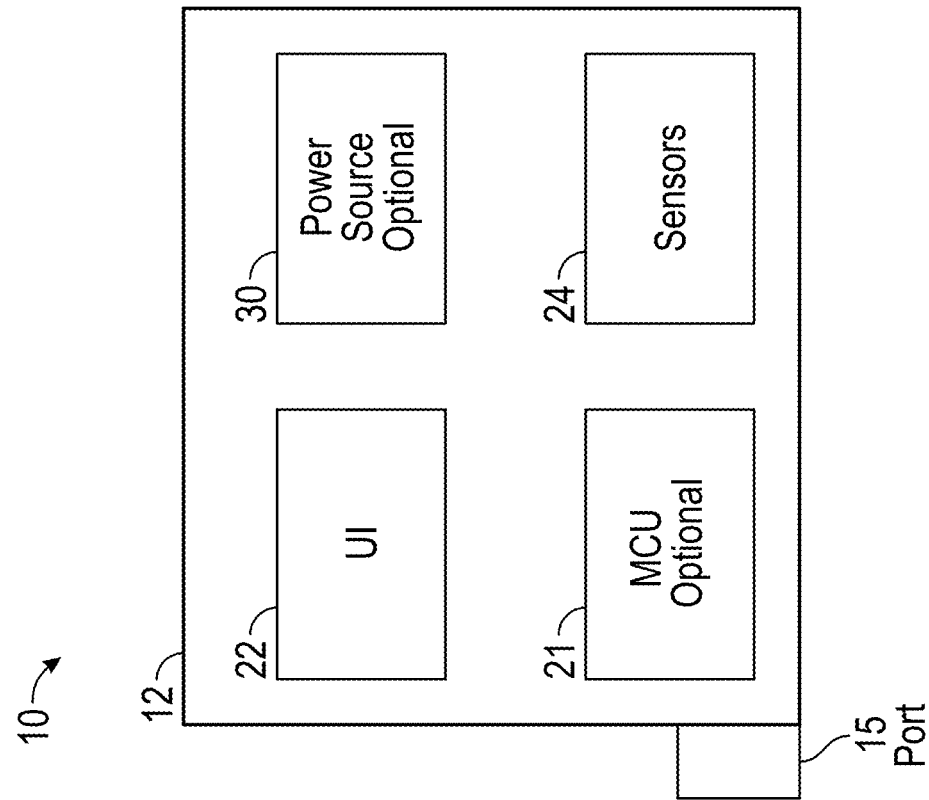
Figure 1B:
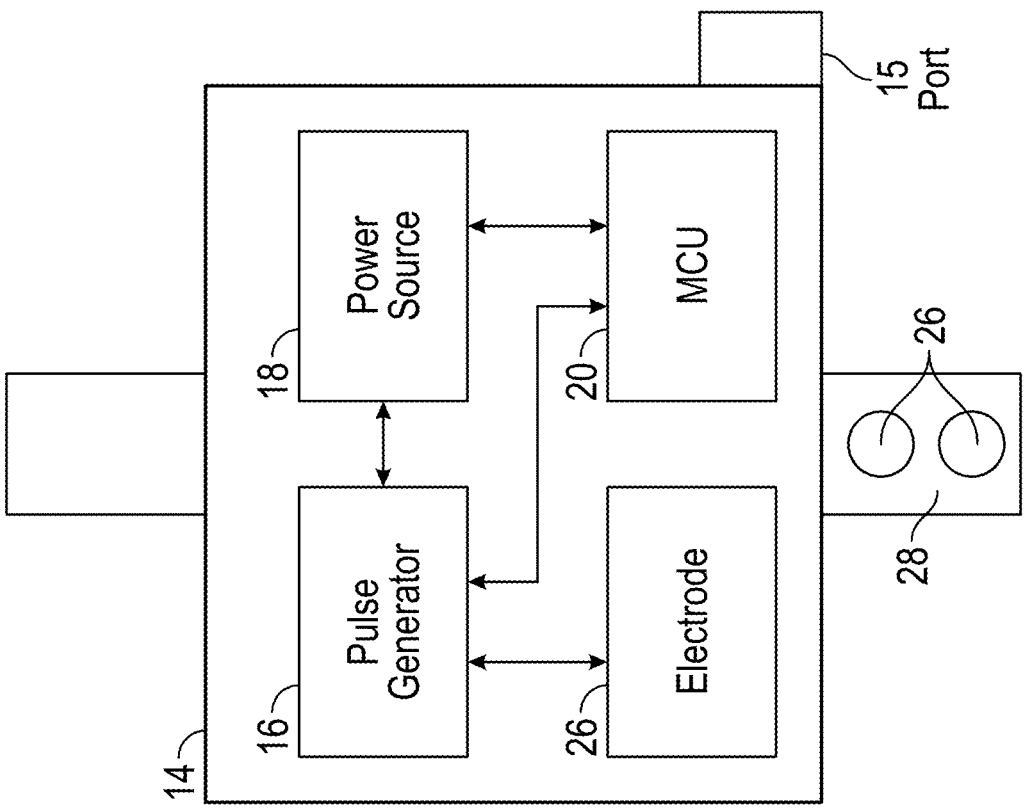
Figure 2A:
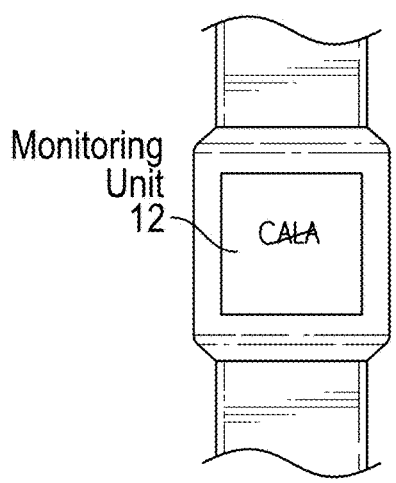
FIGS. 2A-2D illustrate an embodiment of a two part system with a single monitoring unit and a plurality of therapy units.
Figure 2B:
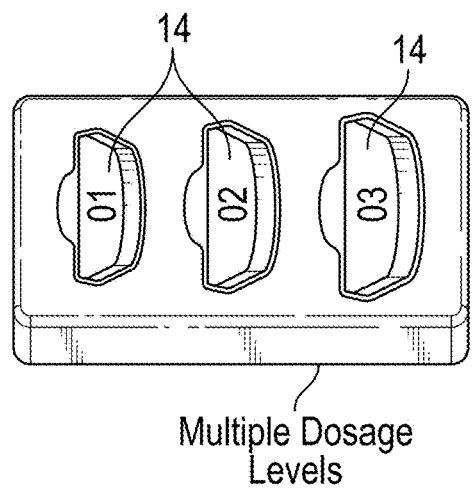
Figure 2C:
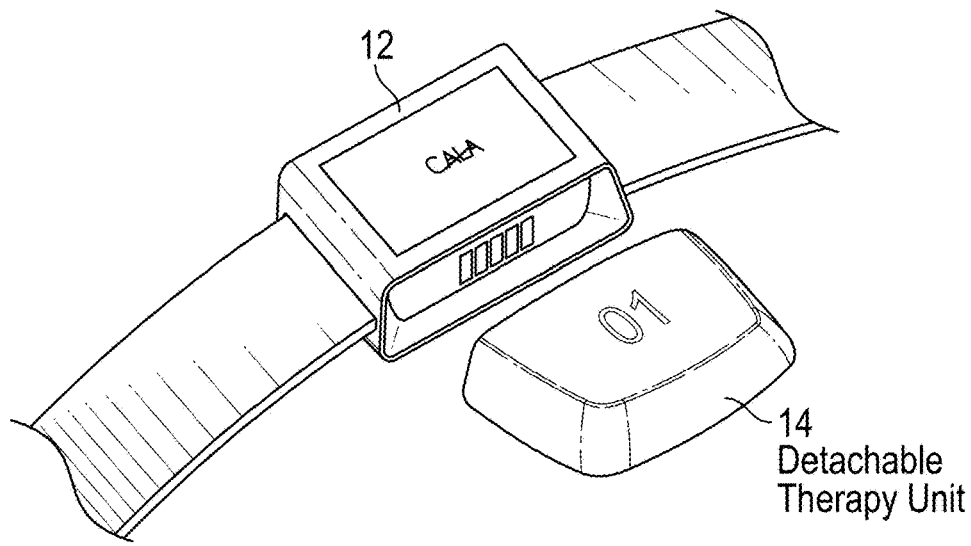
Figure 2D:
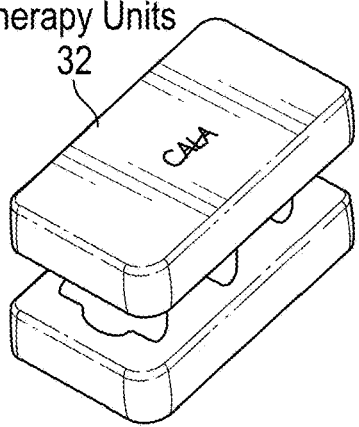

In some embodiments, as shown in FIG. 1B, the therapy unit 14' may directly make contact with the wearer's skin and have the capability to provide electrical stimulation of targeted nerves, such as the median and radial nerves or the tibial nerve or the sacral nerve, using electrodes 26. In some embodiments, the therapy unit 14' has 2 or 3 electrodes, or at least 2 or 3 electrodes. These electrodes 26 may be located on the housing of the therapy unit 14' and/or the therapy unit 14' may also have a band 28 or securement feature with electrodes 26. In some embodiments, when the therapy unit 14' has electrodes 26, the wearable monitor unit 12' does not have electrodes. In some embodiments, both the monitor unit and the therapy unit can have electrodes. As above, the therapy unit 14' can have a stimulator 16, power source 18, and microcontroller 20. The wearable monitor unit 12' can have a user interface 22 and one or more sensors 24 and, optionally, a power source 30 and microcontroller 21. In some embodiments, when the monitor unit has a power source 30 and/or a microcontroller 21, the therapy unit does not have a power source and/or a microcontroller. In some embodiments, the wearable monitor unit 12' is a smart watch, such as the Apple Watch or an Android based smart watch, with an application that allows the smart watch to communicate with the therapy unit and perform as a monitor unit. In some embodiments, the wearable monitor unit 12' can communicate with the therapy unit 14' wirelessly, and one or both of these devices can also communicate with an external computing device wirelessly. In some embodiments, one or both of the wearable monitor unit 12' and the therapy unit 14' can have a data/power port 15. In some embodiments, the wearable monitor unit 12 and the therapy unit 14' can be connected to each other through the data/power ports 15.

In some embodiments, the sensors can be located in or on the therapy unit instead of the monitoring unit. In some embodiments, the sensors can be located on both the therapy unit and the monitoring unit.

In some embodiments, the monitor unit can instead be carried by the user in, for example, the user's hand or pocket, rather than be worn. For example, a monitor unit carried by the user can be a smart phone, such as an Android smartphone or iPhone.

In some embodiments, the two part system or the monitor unit may instruct the user to perform an action, such as draw, write, or hold an object, or to remain still or to attempt to remain still while the wearable monitor unit takes a measurement with one of the sensors.

In some embodiments, the user interface can include a display. In some embodiments, the display can be a touch screen display. In some embodiments, the user interface can include one or more buttons and/or a keyboard.

In some embodiments, the electrodes can be dry-contact (e.g., fabric, metal, silicone or any other plastic impregnated with conductive fillers, or a combination), use a conductive gel (e.g., hydrogels), or have a wet electrode surface (e.g., a sponge with water or conductive liquids or gels), or have fine micro needles, for example. In some embodiments, the electrodes can have a foam backing as further described below.

In one embodiment of the system, the stimulation is provided by implanted electrodes that stimulate nerves in the wrist, such as the median nerve or radial nerve, or other nerves in a plurality of other locations, such as nerves in the leg like the tibial nerve, or nerves in the back like the sacral nerve. The implantable electrode may be powered by a rechargeable battery housed within the implant and recharged wirelessly from an external power source.

In another embodiment of an implanted electrode that stimulates the nerve, the implanted electrode is powered by an external therapy unit, and the stimulation pulse is directly coupled to the electrode and nerve using capacitive or inductive coupling.

In some embodiments, the monitor unit can be a wearable tremor monitor having a housing with a user interface. The housing use a plurality of sensors to collect, store, and analyze biological measures about the wearer including, but not limited to, motion (e.g., accelerometers, gyroscopes, magnetometer, bend sensors), muscle activity (e.g., EMG using electrodes), cardiovascular measures (e.g., heart rate, heart rate variability using electrodes to measure ECG, heart rhythm abnormalities), skin conductance (e.g., skin conductance response, galvanic skin response, using electrodes), respiratory rate, skin temperature, and sleep state (e.g., awake, light sleep, deep sleep, REM). In particular, studies have shown that increased stress levels can increase tremor in people with Essential Tremor, Parkinson's Disease, and other diseases causing tremor. Thus, using standard statistical analysis techniques, such as a logistical regression or Naïve Bayes classifier, these biological measures can be analyzed to assess a person's state, such as level of stress, which in turn, can serve as a predictor for increases in tremor level. In an early pilot study, patients were asked to perform activities prior to and after a stressful event. In this case, the stressful event was to take a timed math test. In preliminary studies, the patients' amplitude of tremor appeared to increase by about 20% after the stressful timed math test.

In one embodiment of the wearable monitor, the skin interface has an array of microneedles. Microneedles have been shown to measure blood chemistry using electrochemical sensors that can be used to detect specific molecules or ptI levels. Thus the monitoring unit could incorporate microneedles with electrochemical sensors to measure specific chemicals in the blood stream that may affect tremor, such as stress hormones, caffeine, or medications.

In one embodiment of the monitor, a saliva sample is taken with a paper strip placed in the mouth, and saliva chemistry is analyzed by sensors in the wearable monitor or in a standalone analysis unit, for substances that may affect tremor, including stress hormones (e.g., cortisol), caffeine, or medications. The unit could have a light source and photo detectors to analyze the chemistry of the strip. The unit could also communicate with an external processing device, such as a cell phone. The strips could be visually coded to record and store information about the measurement (e.g., time, location, etc).

The wearable tremor monitor can have a microprocessor to analyze biological measures about the wearer to: determine or predict the onset of increased tremor activity, set parameters of the stimulation waveform applied by the therapy unit, and/or adapt the stimulation waveform applied by the therapy unit in real time. Parameters of the stimulation waveform that could be modified based on analysis of biological measures are frequency, amplitude, shape, burst sequence. In some embodiments, the analysis can be performed by a microprocessor on the therapy unit or an external computing device.

One embodiment of the system could centrally store biological measures from multiple wearers on a server system (e.g., the cloud), along with other relevant demographic data about each user, include age, weight, height, gender, ethnicity, etc. Data collected from multiple wearers is analyzed using standard statistical techniques, such as a logistic regression or Naïve Bayes classifier (or other classifiers), to improve prediction of tremor onset by determining correlations between biological measures and other recorded events and onset of increased tremor activity. These correlations are used to set parameters of the stimulation waveform applied by the therapy unit, determine best time to apply stimulation therapy, and/or adapt the stimulation waveform applied by the therapy unit in real time.

In one embodiment of the system, the wearable tremor monitor that automatically detects and records the dosage and consumption of medications to (1) track compliance of the patient; (2) combine with the measurement of tremor activity to assess therapeutic effectiveness, and (3) determine or predict the onset of an increase or decrease in tremor activity. The dosage and consumption of medications can be detected and record in multiple ways, including (1) using visual scanner to record a marking on the pill pack or bottle each time medication is consumed, (2) a smart pill cap with force sensors and a wireless transmitter to detect each time the medication is consumed from a pill bottle, (3) an RFID chip that is of similar size and shape as a pill that is consumed with each dosage of medication that is activated by digestion and communicates with the monitor device, (4) an RFID chip embedded in a sugar pill that is consumed with each dosage of medication that is activated by digestion and communicates with the monitor device, and (5) a pill with a visual encoding that is scanned and recorded by a camera on the monitor unit each time medication is consumed.

In some embodiments, the wearable tremor monitor can have a visual, auditory, tactile (e.g., squeezing band), or vibrotactile cues to notify the wearer of key events based on analysis of biological measures, including, but not limited to, prediction of tremor onset, increase in tremor activity, and/or increase in stress level. The cuing system could also notify the wearer of other predetermined events or reminders set by the wearer. Cuing system is used to (1) communicate information to the wearer, such as onset of increased tremor activity or other predetermined events, in a more discreet, personalized way, without drawing attention from others in social situations.

In some embodiments, the form of the wearable monitor and/or therapy unit could be a wrist band or watch, a ring, a glove, an arm sleeve or arm band, an ear piece/headphone, head band, a necklace or neck band, or a compliant patch.

In one embodiment, the wearable monitor can have a processing unit and memory that collects, stores, processes, and analyzes the biological measures, along with other data input by the wearer.

In some embodiments, the wearable monitor can take user input about events, including diet history, medication history, caffeine intake, alcohol intake, etc. The monitor can use accelerometers to measure specific movements, gestures, or tapping patterns to record user inputs at specific prompts. Other touch sensors, such as resistive strips or pressure sensitive screens, could be used to measure specific gestures to record user inputs. These gesture based measures to record user input minimize the complexity of steps required to input user data into the device. The data can be stored in memory and processed by the processing unit. In some embodiments, the data can be transmitted from the wearable monitor to an external computing device.

In one embodiment, the wearable monitor and/or the therapy unit can connect with other applications, such as calendars and activity logs, to sync and track events or a saved calendar can be saved and stored on the device. In some embodiments, the wearable monitor and/or the therapy unit can communicate with a variety of computing devices, such as a smart phone, a smart watch, a tablet, a laptop computer, or a desktop computer, for example, that have these applications.

In one embodiment, the monitor unit and/or therapy unit can have a OPS or similar device to track the location and assess activity of the wearer. GPS measures can be combined with mapping or location systems to determine context of the wearer's activity (e.g., gym, office, home) or determine changes in elevation during specific activities, such as running or cycling.

In some embodiments as shown in FIGS. 2A-2D, a single monitor unit 12 can be used with a plurality of therapy units 14 having different sizes, shapes, colors, markings and/or capabilities, which includes different battery capacity and power output. Different wearers and usage scenarios may require different amounts of stimulation duration and power, making a smaller or larger therapy unit more desirable and giving the wearer options to meet their needs in different scenarios. In some embodiments, the therapy units 12 can also have different programming, including different stimulation parameters and/or therapies which can be tailored to different types of treatments. For example, one therapy unit can be tailored to treat essential tremor, while another therapy unit can be used to treat Parkinson's disease and another for freezing of gait or overactive bladder. In some embodiments, the therapy units can each be tailored to provide different intensity of treatments, such as one unit for light treatment of essential tremor and another for heavy and aggressive treatment of essential tremor. The different features and capabilities of the therapy units can correspond to the different sizes, shapes, color, and/or markings. A carrying case 32 can be used to hold a set of therapy units, such as a set of therapy units to treat essential tremor that differ in battery capacity and power output or some other feature.

In one embodiment, the therapy units have a unique charging station that can simultaneously charge multiple therapy units. The charging station could have a custom direct electrical connection to the therapy units or could charge the therapy units wirelessly in a close proximity. Similarly, in some embodiments, the charging station can charge the monitoring units in a similar manner.

In one embodiment, the wearable monitor can track parameters about stimulation provided by the therapy unit, including time of stimulation, duration of the stimulation session, and power used by the therapy unit. This data can be stored on memory in the wearable monitor, processed by the wearable monitor, and/or transmitted to an external computing device.

In one embodiment, the therapy unit can use switches or an electrical sensor to detect connection of electrodes: (1) to ensure proper and unique electrodes are being installed (i.e., not using a different or incorrect type of electrode) communicating a unique code, for example via RFID, an encoded EEPROM chip, a resistance or capacitance based ID, a binary identifier, or a surface pattern (2) to regulate the number of uses for each electrode to prevent over use, and (3) to prevent the usage of the device without an electrode to prevent small shock. In some embodiments, the therapy unit and/or the monitor unit can have an identifier that can be transmitted to and be received by each other or to an external computing device. The identifier can allow one unit to determine the features, capabilities, and/or configuration of the other device, including the electrode configuration described above, so that the appropriate treatment parameters can be used, and also the usage life or expiration of the component, which can be based on voltage measurements, time, number of therapy sessions, or other parameters. In some embodiments, instead of using an identifier, the features, capabilities, and/or configuration of one device can be transmitted to the other device, either directly from one device to the other device, or through entry into the user interface, or through an external computing device.

Other components of the therapy system, including the band, the therapy unit, the monitoring unit, the skin interface, can each have one or more identifiers that performs the functions described above. These identifiers can encode a variety of information as described herein, as well as predetermined dosing regimens, initialization routines, calibration routines, or specific parameters. The identifiers may be associated with a lookup table that stores the encoded information.

In some embodiments, the wearable monitor and/or the therapy unit can communicate with an external computer or device (e.g., tablet, smartphone, smartwatch, or custom base station) to store data. Communication between the monitor and external device can be a direct, physical connection, or with a wireless communication connection such as Bluetooth or GSM or cellular.

In one embodiment of the device, the therapy unit has an array of electrodes and one or more sensors, such as pressure sensors, between the therapy unit and the wearer's wrist to measure pressure of contact of the skin interface at and/or around the electrodes. This pressure data can be analyzed to determine which electrodes in the array to stimulate to target the appropriate nerves or to detect changes in skin contact due to motion or other conditions and switch stimulation of the electrode array to the optimal location. These methods are used to (1) assess poor contact of electrodes, and (2) adjust amplitude of stimulation based on pressure measurement.

Increasing contact pressure between the device and the wearer's skin and/or stimulating with electrodes with an adequate contact pressure or above a contact pressure threshold could: (1) increase the surface area of contact, which reduces discomfort, (2) activate deep somatic pain (i.e., type C) peripheral nerve fibers, which could reduce discomfort from stimulation, which activates superficial pain (i.e., type A delta) fibers, (3) reduce the stimulation amplitude needed because it improves stimulation of the targeted nerve (e.g., the electrode is physically closer to the nerve by pressing it), or (4) reduce the effect of skin motion.

In one embodiment, the therapy unit has the form of an inflatable wrist band, which is made of a pliable, airtight material. A small pump is actuated or activated by the user to fill the bladder with air and increase pressure to increase the surface area of contact, which reduces discomfort. In some embodiments, the pump is integrated into the wrist band and can be either mechanically actuated by the user or electrically powered by a battery. In other embodiments, the pump can be separate from the wrist band.

In one embodiment, the pressure is provided by a compliant material within the band, such a soft open cell foam or an array of mini springs (e.g., pogo pins).

Figure 3:
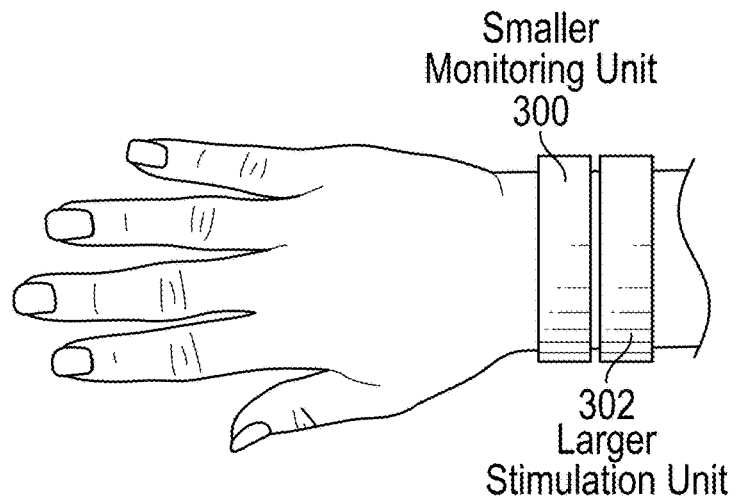
FIG. 3 illustrates an embodiment of a two part stimulation where both the monitoring unit and the therapy unit are bands.

In one embodiment of the device as shown in FIG. 3, the monitor unit 300 and the therapy unit 302 have the form factor of two distinct wrist bands that can connect to each other. The monitor unit 300 is the primary wrist band, and the therapy unit 302 is attached secondarily, as needed, into the monitor unit 300. Alternatively, the therapy unit 302 may remain separate of the monitor unit 300 and can communicate wirelessly with each other.

Figure 4A:
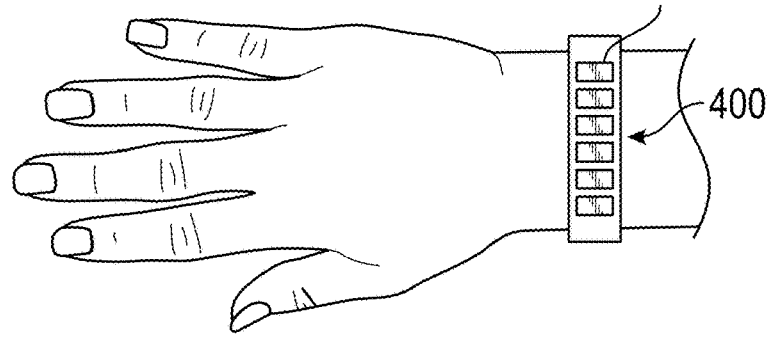
FIGS. 4A and 4B illustrate an embodiment of a touch sensor array that can be used to select electrodes from a corresponding electrode array.
Figure 4B:
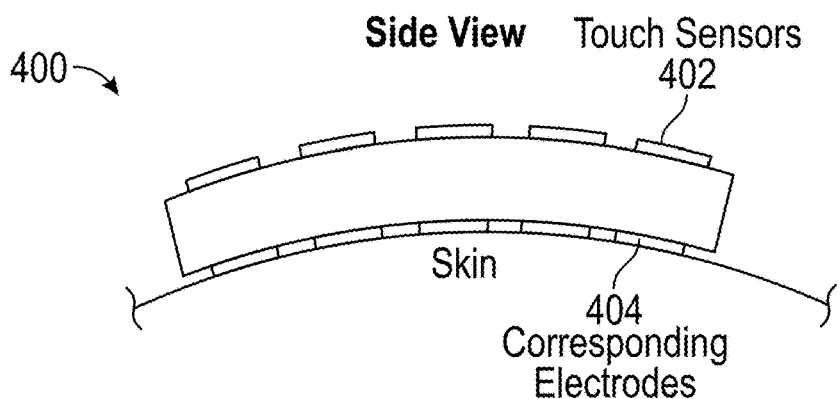

In one embodiment as shown in FIG. 4, the therapy unit 400 has a touch sensor array 402 that corresponds to an electrode array 404. When attached to the wearer, the electrode array 404 is contacting the wearer's skin, and the touch sensor array 402 is on the opposite, outer part of the therapy unit 400. The wearer can use the touch sensor to indicate the preferred location of stimulation of the therapy unit 400 by touching the desired location on the touch sensor. For example, touching one touch sensor in the touch sensor array 402 activates the corresponding electrode in the electrode array 404, allowing the user to easily select which electrodes of the electrode array 404 to use for stimulation.

Figure 5:
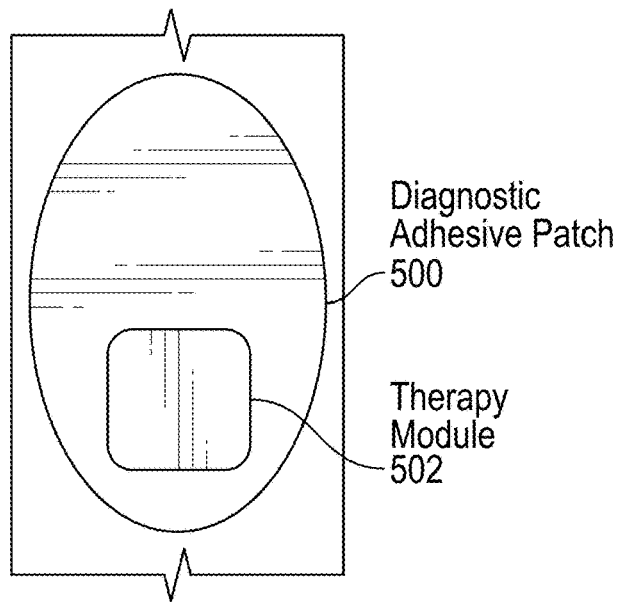
FIG. 5 illustrates an embodiment of a two part system formed from a monitoring patch and therapy unit.

In some embodiments as shown in FIG. 5, the two part system can include a monitor unit that is a wearable monitor patch 500 with at least two electrodes or at least two separate patches each with an electrode that adheres to the skin via an adhesive, surface adhesion of the material, or microneedles. The monitor patch also can include a current spreader at the skin interface to deliver electrical energy to the skin more evenly. Generally, it is desirable to have at least two electrodes or patches in order to have a ground electrode to adequately deliver energy to nerves transcutaneously. The system can also have a therapy unit 502 that houses the power source, signal generator, and microcontroller for electrical stimulation through the monitor patch 500 to which it attaches via a metal snap, a magnet or other electrical connector.

In one embodiment of the above, the therapy unit wirelessly powers the monitoring patch.

Figure 6:
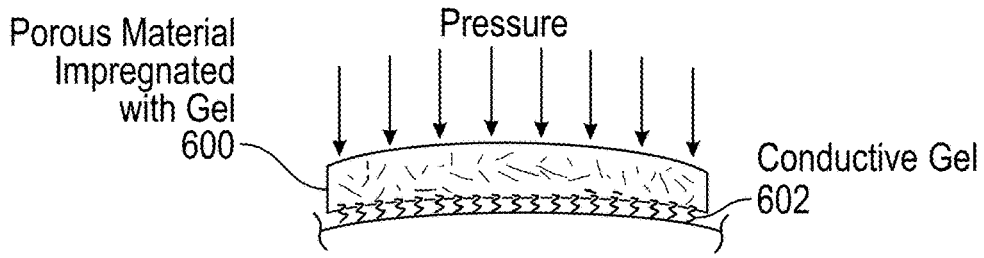
FIGS. 6-8 illustrate various embodiments of skin interfaces that incorporate a conductive gel.

In some embodiments as shown in FIG. 6, the skin interface at and/or around the electrode of the monitoring unit and/or therapy unit is provided by a porous material 600, such as a foam polymer, that is impregnated with conductive gel 602. In some embodiments, the foam polymer is made of a conductive polymer. In other embodiments, the foam polymer is made of a nonconductive polymer. In some embodiments, the foam material is flexible and compressible and can conform to the patient's skin. The conductive gel is disposed within the pores of the porous material, and as pressure is applied to the porous layer by for example the housing and electrode, conductive gel is pushed and squeezed out through the pores of the porous material and onto the wearer's skin as the foam material is compressed. Pressure can be applied to the porous material by squeezing and/or pushing on the housing of the therapy unit against the skin by the wearer, or by a screw mechanism, or some other mechanism that tightens the outer housing to compress the gel layer, or by tightening a band that fastens the therapy unit to the patient.

Figure 7:
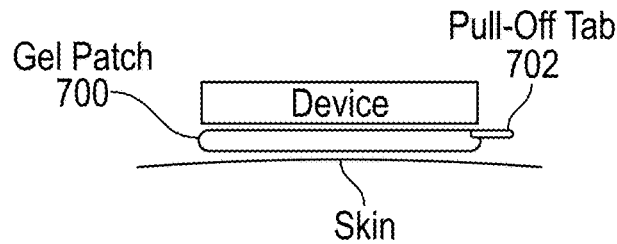

In some embodiments as shown in FIG. 7, the skin interface of the housing and electrodes of the therapy unit and/or monitoring unit can include a thin gel patch 700 covered by a protective liner with a pull-off tab 702 that slides between and/or is positioned between the device and the wearer's skin. The protective liner can be removed using the pull-off tab 702 to expose the conductive gel. The gel patch is electrically conductive and creates and/or improves an electrical connection between the skin and the electrodes to deliver electrical energy to the wearer's skin.

Figure 8:
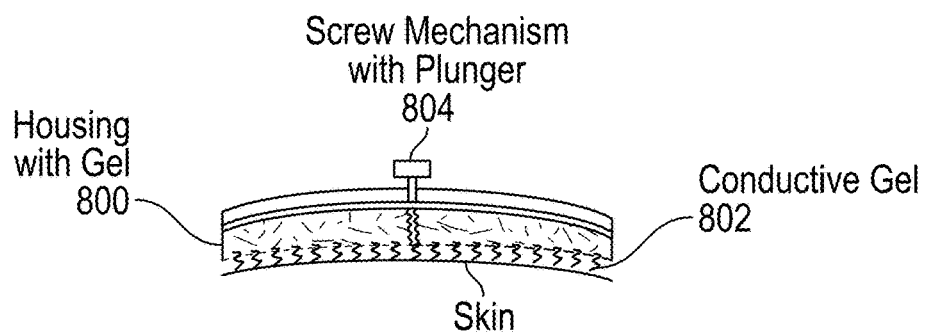

In some embodiments as shown in FIG. 8, the housing of the therapy unit and/or monitoring unit and/or structure with the electrodes, such as a band, can include a reservoir 800 filled with a conductive gel 802 and a plurality of pores or channels at the skin interface through which the conductive gel in the reservoir can be dispensed onto the wearer's skin to improve the skin interface for stimulation. The gel can be dispensed with a screw mechanism 804 or plunger or button or collapsible reservoir or other mechanism that pushes gel out of the reservoir through small channels or pores onto the wearer's skin.

In one embodiment, the system helps the wearer relax—by using a cuing system to remind the wearer to relax or practice relaxation techniques. The cuing can be auditory, visual, or tactile. Also, the system can provide feedback about the wearer's stress level that gives reinforcement that relaxation techniques are working.

Figure 9A:
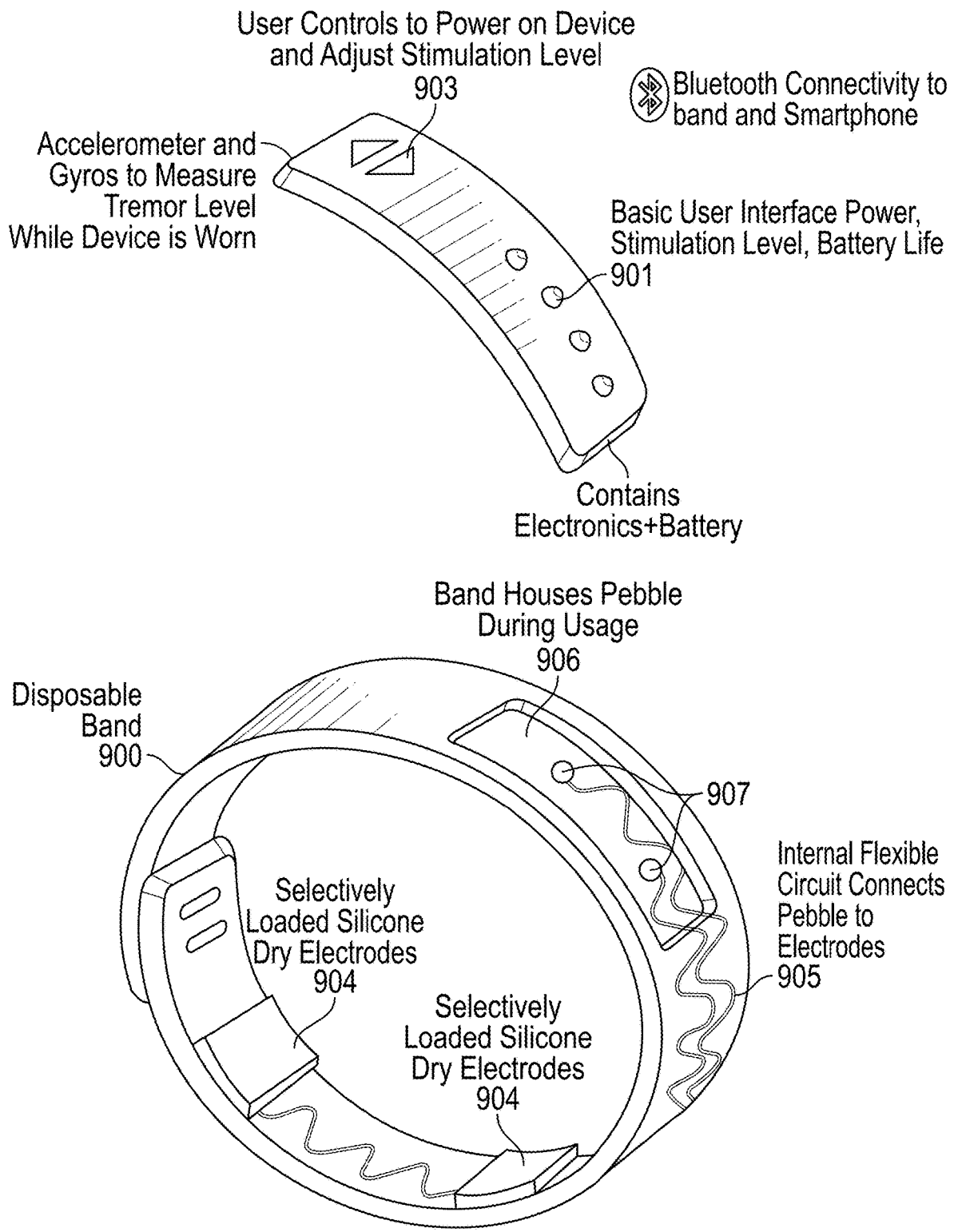
Figure 9F:
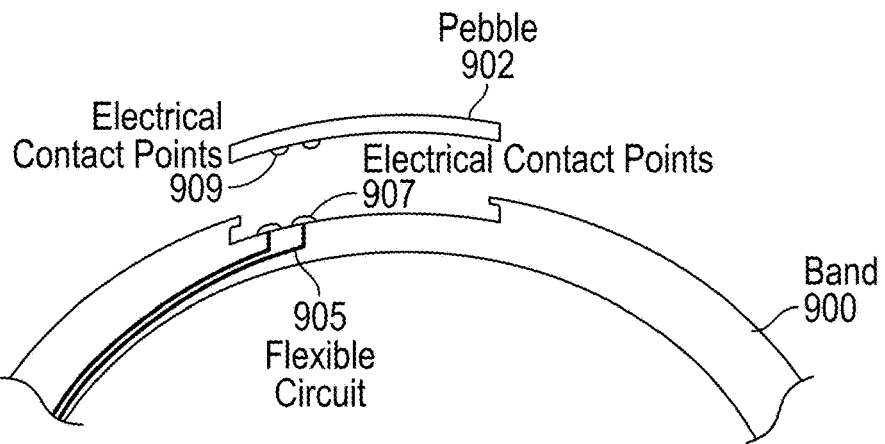
Figure 9G:
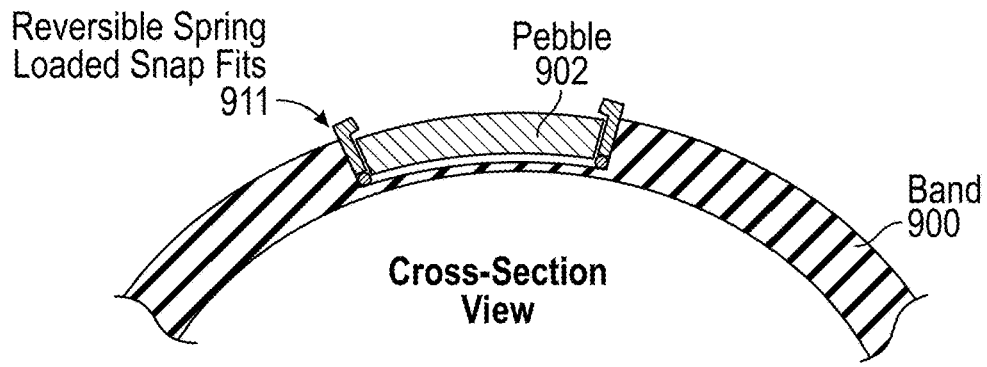
Figure 9H:
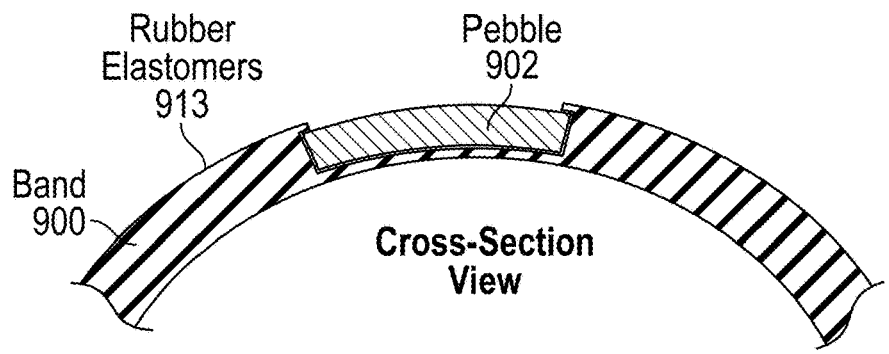
Figure 9I:
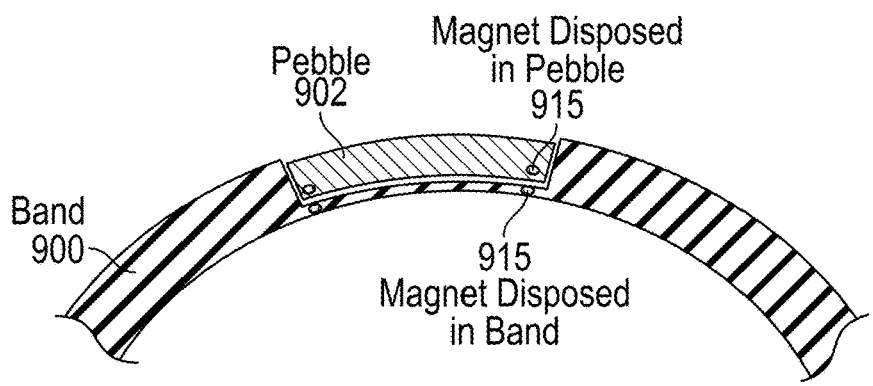

FIGS. 9A-9I illustrates another embodiment of a two part therapy system that includes a disposable band 900 and a therapy unit 902 that can be reversibly attached to the disposable band 900. The disposable band 900 can have two or more electrodes 904 disposed on a skin facing or inside surface of the band and a receptacle 906 or receiving portion for reversibly receiving the therapy unit 902. Within the band 900 are wires and/or conductive traces that form a flexible circuit 905 that runs from the electrodes 904 to the receptacle 906 for electrically connecting the electrodes 904 to the therapy unit 902 when the therapy unit 902 is disposed in the receptacle 906. In some embodiments, the wires and/or conductive traces of the flexible circuit 905 are arranged in a wave or undulating pattern in order to improve its ability to flex. In some embodiments as shown in FIG. 9F, the receptacle 906 can have one or more electrical contact points, such as one or more pin holes 907, for receiving one or more complementary electrical contacts, such as pins 909, from the therapy unit 902. The flexible circuit 905 can extend to the pin holes 907 such that an electrical connection is formed when the pins are inserted into the pin holes. In some embodiments, as shown in FIGS. 9G-9I, the receptacle 906 can have a clip, retaining lip, magnet, a snap fit, a twist fit, a hook, a latch, a sliding mechanism, or other securement feature for reversibly securing the therapy unit 902 to the band 900. FIG. 9G illustrates clips 911 that may or may not be spring loaded to form a snap fit around the therapy unit 902. FIG. 911 illustrates a flexible lip 913 around the opening of the receptacle that can be used to retain the therapy unit 902 after it is inserted into the receptacle 906. FIG. 9I illustrates magnets 915 that can be placed in complementary positions in the therapy unit 902 and the receptacle. In some embodiments, the clip, magnet, snap fit mechanism, twist fit mechanism, hook, or other securement feature is made of metal or some other conductive material and can be electrically connected to the electrodes via the wires and/or conductive traces. The electrodes 904 can be dry electrodes or can be coated with a conductive gel.

In some embodiments, the therapy unit 902 can include a battery, which may be rechargeable, and electronics to deliver electrical stimulation through the electrodes to the patient's nerves. The electronics can include a stimulator and a microcontroller, and may also include memory and one or more sensors, such as one or more accelerometers and gyroscopes as described herein. In some embodiments, the device is able to sense the impedance of the electrodes in order to assess the integrity of the electrode to skin interface. In some embodiments, there can be an electrical indication (e.g. reading of a chip, pushing in of a sensor on the connector, etc.) to detect integrity of the connection between the band and the therapy unit. In some embodiments, the therapy unit 902 can have one or more LEDs, mini OLED screens, LCS, or indicators 901 that can indicate the status of the therapy unit 902, such as whether the therapy unit 902 is connected to the band 900, the power remaining in the battery of the therapy unit 902, whether a stimulation is being delivered, the stimulation level, whether data is being transmitted, whether a sensor measurement is being taken, whether a calibration routine is being performed, whether the therapy unit 902 is initializing, whether the therapy unit 902 is paired with another device such as a smart watch and/or smart phone, whether the battery is being charged, and the like. In some embodiments, the therapy unit 902 may also include a user interface 903, such as one or more buttons.

FIG. 9B illustrates a kit that can be sent to a user. The kit can contain a plurality of bands 900 of different sizes, shapes, colors, etc to accommodate patients having different wrist sizes or other body part sizes, such as ankles, arms, fingers, and legs and to accommodate different types of connected accessories like secondary displays (e.g. smart watch, iwatch). In some embodiments, the kit has three bands. Additionally, the kit can contain one or more electronic units 902. If multiple electronic units 902 are provided in the kit, the battery capacity of the different electronic units 902 can be different to accommodate different usage types. For example, a relatively low capacity battery can be used for on-demand stimulation, while a relatively high capacity battery can be used for automated and/or responsive stimulation driven by the microcontroller. In some embodiments, only a single electronic unit is provided. In other embodiments, a plurality of electronic units are provided while a single band is provided. The kit may also include a charger 908 to charge the therapy unit 902. In some embodiments, the charger 908 can inductively charge the therapy unit 902. In other embodiments, the charger 908 can charge the therapy unit with a charge cable that can be inserted into a power port in the therapy unit. In some embodiments, the therapy unit 902 can be docked with the charger 908 for charging.

FIG. 9C illustrates an embodiment where a smart watch 910, such as the Apple Watch, is reversibly or permanently fastened to a band 900, which may also have a therapy unit 902. In some embodiments, the smart watch 910 may provide a display and a user interface for the therapy unit 902. The smart watch 910 may communicate with the therapy unit 902 wirelessly, such as through Bluetooth or WiFi, or through a direct connection through a data port in the smart watch and a data port in the therapy unit 902. In some embodiments, the electronic unit 902 and/or smart watch 910 may communicate with a smart phone 912, as described herein, to transmit data or to update the software and/or stimulation parameters on the therapy unit 902 and/or smart watch 910. In some embodiments, the band 900 and therapy unit 902 are permanently affixed or integrated together while the smart watch 910 is reversibly attachable to the band 900. The smart phone 912 and/or the smart watch 910 can include an application, which may be downloaded through the cloud or a computer, configured to interface with the therapy unit 902.

FIGS. 9D and 9E illustrate that the wearable two part system can be worn and used throughout the day. When the power remaining in the battery of the therapy unit is low, the therapy unit 902 can be recharged with the charger 908. Charging can be performed at night or whenever the battery is low or when desired. In some embodiments, the therapy unit can be removed from the band before charging. In some embodiments, the user can swap a low charge therapy unit with a high charged therapy unit so that the user can always be wearing a therapy unit.

In some embodiments, the kit illustrated in FIG. 9B can be used as a diagnostic trial kit. The patient can initially wear the therapy system for about 1 to 14 days, or about 1 week, or for a predetermined length of time, with the therapy turned off so that no electrical stimulation is provided to the patient during this time. This initial period is used to collect data with the sensors in the therapy unit and/or band in order to characterize the tremor or other disease. The sensor data can be stored in memory in the therapy unit, and/or can be transmitted through a network to the cloud or a server or to another computing device, which can be accessed by the patient's physician.

Following the data collection phase, the patient can turn on the therapy function on the therapy unit and perform patient-directed tasks after and/or while being given one or more therapy treatments, which may be stored on the therapy unit, in order to identify how well the patient is responding to the various treatments. The patient response data can also be stored on memory and/or transmitted through a network or to another computing device, which can be accessed by the patient's physician.

In some embodiments, the patient can return the kit to the physician or manufacturer of the kit, and data can be retrieved from the system and transmitted to the patient's physician.

Using the data from system, the physician can characterize the patient's tremor or other disease, generate a diagnosis, and determine the appropriate treatment for the patient, which may include selection of the appropriate therapy system and stimulation parameters.

Figure 10:
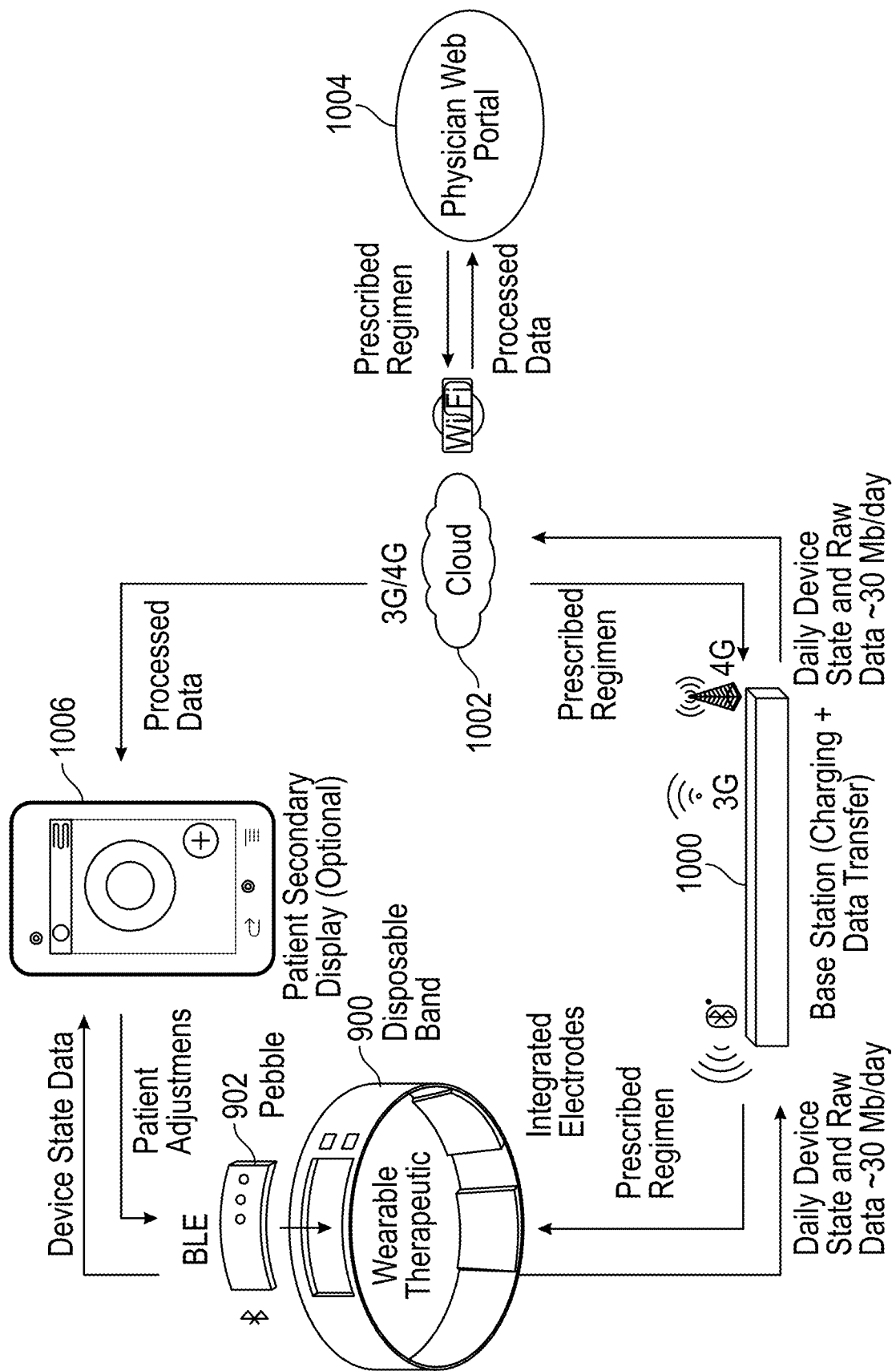
FIG. 10 illustrates an embodiment of the wearable therapy system that uses the cloud to receive and transmit data between the therapy system and a physician.

FIG. 10 illustrates an embodiment of a system for treating tremor or another disease or condition using a wearable therapy device. As described above, the therapy device may have two parts, a band 900 and therapy unit 902. A base station 1000, which may replace the charger in the kit described above, can be used to both charge the therapy device and to receive and transmit data to the therapy device and to the cloud 1002. Communication between the base station 1000 and the therapy device can be wireless, such as through Bluetooth and/or WiFi, and communication between the base station 1000 and the cloud 1002 can be through a cellular network, using a 3G or 4G connection, or through a wired connection to the internet, using DSL or cable or ethernet, for example. A physician or other user can view and/or retrieve data stored on the cloud 1002 using an online portal or a physician web portal 1004. In addition, the physician can prescribe and/or modify a treatment regimen on the therapy unit 902 through the cloud 1002 and base station 1000 using the web portal 1004.

In some embodiments, the base station 1000 is used to receive and transmit relatively large amounts of data that may require a high bandwidth, such as the transmission of raw data from the therapy device, which may be about 10 to 100 Mb/day, or about 10, 20, 30, 40, or 50 Mb/day. In some embodiments, the data may be stored in memory in the base station 1000 and transmitted at another interval, such as weekly or twice weekly, with a scaling up of the bandwidth of transmission. The high bandwidth transmission of the raw data can occur daily while the therapy device is being charged, such as at night during a regular charging period. In some embodiments, the raw data can be processed by the cloud and/or the physician into processed data and sent back to the therapy device.

In some embodiments, the system may optionally include a portable computing device 1006, such as a smart phone or tablet, to provide a secondary display and user interface for the patient and to run applications to more easily control the therapy device and view the raw and processed data. The portable computing device can be used to make patient or physician adjustments to the therapy device, such as adjusting the stimulation parameters and dosing, and can receive device state data from the therapy device, which includes data relating to the device, such as when the device was used, errors, therapy parameters such as amplitude and when they were set and delivered. In some embodiments, the portable computing device 1006 can receive processed data from the cloud 1002 through a cellular network and/or through an internet connection using WiFi, for example.

Figure 11:
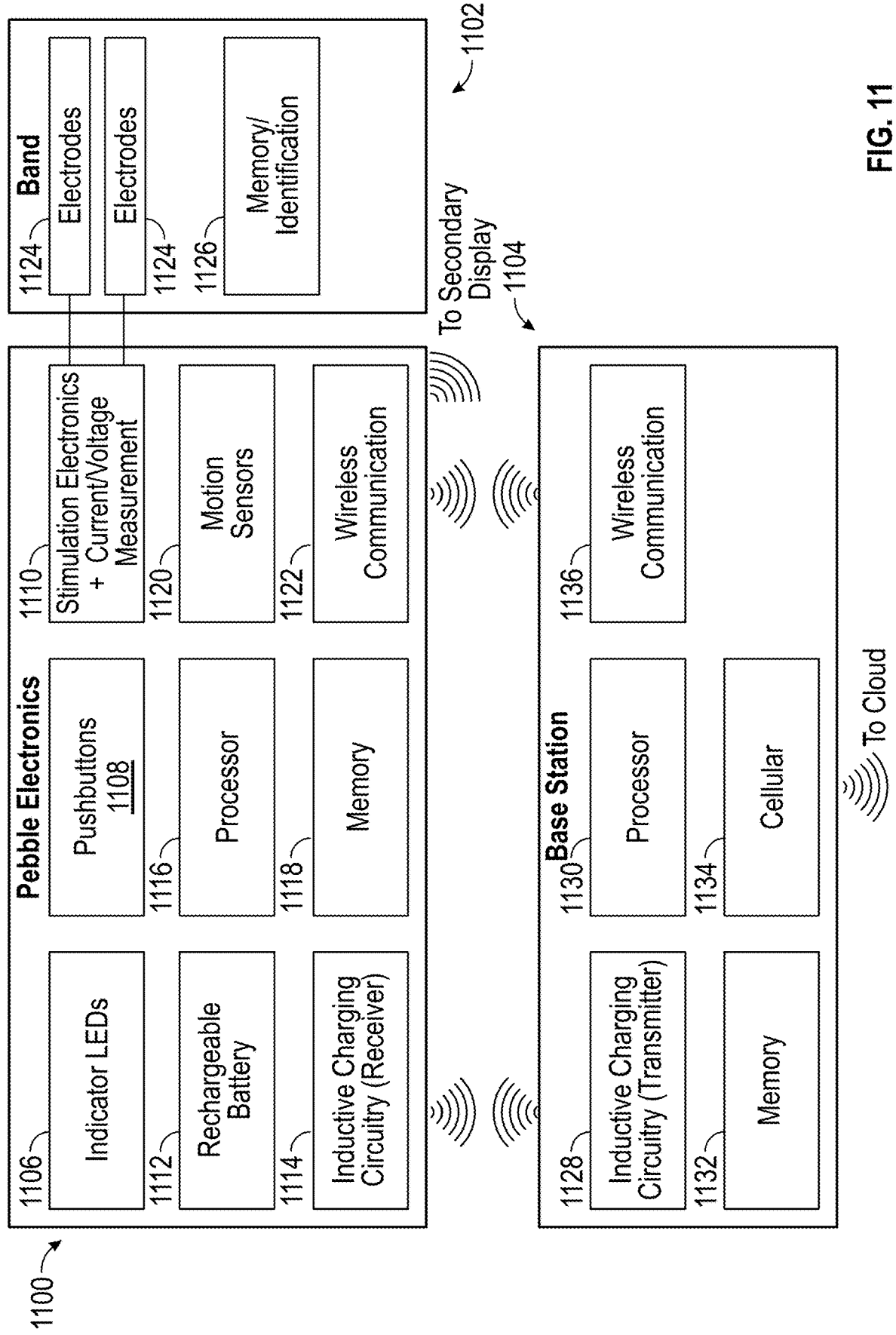
FIG. 11 is a block diagram that illustrates the individual components of the therapy unit, band, and base station shown in FIG. 10.

FIG. 11 illustrates the various components that can be included in a therapy unit 1100, band 1102, and base station 1104. These components are described in detail above and also below as one particular embodiment. For example, the therapy unit 1100 include one or more indicators 1106, which can be LEDs, and a user interface 1108, which can be push buttons, for example. The therapy unit 1100 can also have a stimulator 1110 with stimulation electronics and may include the capability to measure current and voltage. The therapy unit 1100 can also have a battery 1112, which may be rechargeable and can be recharged using charging circuitry 1114, which may be inductive. The therapy unit 1110 may further include a processor 1116 and memory 1118 to store and execute programs and instructions to accomplish the functions described herein. The therapy unit 1110 may also include sensors 1120, such as motion sensors, and a communications module 1122, which may be wireless and can communicate with the base station 1104 and/or a secondary display/computing device.

The band 1102 can have electrodes 1124 and may also include memory to store identification information or may include some other form of identifier 1126 as described herein.

The base station 1104 can include charging circuitry 1128, which may also be inductive and can transmit power to the complementary charging circuitry 1114 on the therapy unit 1100. The base station 1104 can also have a processor and memory for storing and executing instructions and programs. The base station 1104 can further include a communication module 1132, which may be cellular, to communicate with the cloud, and another communication module 1134, which may be wireless and used to communicate with the therapy unit.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A system for treating tremor of a patient, the system comprising:
    a band comprising a first surface configured to contact skin of the patient, and comprising at least two skin electrodes, and a second surface opposite the first surface, the second surface comprising at least two receiving contacts and the band further comprising a first electrical circuit configured to be in electrical communication with both the at least two skin electrodes and the at least two receiving contacts; and
    a detachable therapy unit comprising:
        a second electrical circuit;
        one or more sensors in electrical communication with the second electrical circuit, the one or more sensors configured to measure data from the patient;
        a stimulator configured to generate an electrical stimulation, the stimulator in electrical communication with the second electrical circuit;
        at least two therapy unit electrodes that are configured to receive the electrical stimulation from the stimulator, the at least two therapy unit electrodes configured to connect to the at least two receiving contacts, thereby forming an electrical pathway between the stimulator and the at least two skin electrodes;
        a controller configured to control the generation of the electrical stimulation by the stimulator; and
        a power source in electrical communication with the second electrical circuit;
    wherein the detachable therapy unit is configured to be reversibly attached to the band.

2. The system of claim 1, wherein the band further comprises one or more identifiers.

3. The system of claim 2, wherein the one or more identifiers are associated with stimulation parameters and/or usage life information.

4. The system of claim 1, further comprising a base station configured to charge the power source.

5. The system of claim 4, wherein the base station is further configured to receive and transmit data to and from the detachable therapy unit and to and from a cloud computing network.

6. The system of claim 5, further comprising an online portal configured to access the data stored on the cloud computing network.

7. The system of claim 1, further comprising an online portal configured to provide information and parameter changes back to the detachable therapy unit.

8. The system of claim 1, further comprising a portable computing device with a user interface and a display, wherein the portable computing device is configured to wirelessly communicate with the detachable therapy unit and to receive data from the cloud computing network.

9. The system of claim 1, wherein the detachable therapy unit further comprises a user interface.

10. The system of claim 1, wherein the controller is configured to control the generation of the electrical stimulation by the stimulator based on data measured by the one or more sensors.

11. A system for stimulating at least one nerve of a patient, the system comprising:
a wearable band comprising:
a skin facing surface configured to be in contact with skin of the patient, and a surface opposite the skin facing surface, the surface opposite the skin facing surface comprising at least two receiving contacts;
a first electrical circuit; and
at least two transcutaneous electrodes on the skin facing surface,
wherein the first electrical circuit is configured to electrically connect the at least two transcutaneous electrodes with the at least two receiving contacts; and
a first therapy unit comprising:
a first power source;
a first stimulator powered by the first power source, the first stimulator configured to generate an electrical stimulation that is delivered through the at least two transcutaneous electrodes of the wearable band;
at least two electrical contacts configured to connect to the at least two receiving contacts of the wearable band and form a second electrical circuit between the first stimulator and the at least two transcutaneous electrodes;
one or more sensors configured to measure data from the patient; and
a first controller configured to control the generation of the electrical stimulation by the first stimulator based on data measured by the one or more sensors;
wherein the first therapy unit is reversibly attachable to the wearable band.

12. The system of claim 11, further comprising a second therapy unit, the second therapy unit comprising:
a second power source, wherein the second power source of the second therapy unit has more electrical capacity than the power source of the first therapy unit;
a second stimulator powered by the second power source, the second stimulator configured to generate an electrical stimulation that is delivered through the at least two electrodes of the wearable band; and
a second controller configured to control the generation of the electrical stimulation by the stimulator based on data measured by the one or more sensors;
wherein the second therapy unit is reversibly attachable to the wearable band.

13. The system of claim 11, wherein the one or more sensors are configured to measure motion data.

14. The system of claim 13, wherein the controller is configured to:
determine a tremor frequency, amplitude, and/or phase from the motion data; and
control the generation of the electrical stimulation by the first stimulator based on the determined tremor frequency, amplitude, and/or phase.

15. A system for modulating at least one nerve of a patient, the system comprising:
a wearable unit comprising:
a first surface configured to be in contact with skin of the patient and a second surface opposite the first surface, the first surface comprising at least two transcutaneous electrodes and the second surface comprising at least two receiving contacts;
an electrical circuit in electrical communication with the at least two transcutaneous electrodes and the at least two receiving contacts; and
a therapy unit comprising:
a stimulator configured to generate an electrical stimulation;
at least two therapy unit electrodes that are configured to receive the electrical stimulation from the stimulator;
a user interface;
one or more sensors configured to measure data from the patient;
a controller configured to control the generation of the electrical stimulation by the stimulator based on data measured by the one or more sensors; and
a power source disposed within the wearable unit or the therapy unit;
wherein the therapy unit is reversibly attachable to the wearable unit.

16. The system of claim 15, wherein the wearable unit is a smart watch.

* * * * *